(12) United States Patent
Nykiforuk et al.

(10) Patent No.: US 6,552,250 B1
(45) Date of Patent: Apr. 22, 2003

(54) DIACYLGLYCEROL O-ACYLTRANSFERASE

(75) Inventors: Cory L. Nykiforuk, Coaldale (CA); André J. Laroche, Lethbridge (CA); Randall J. Weselake, Lethbridge (CA)

(73) Assignee: Her Majesty the Queen in right of Canada as represented by the Minister of Agriculture and Agri-Food, Lethbridge (CA)

( * ) Notice: Subject to any disclaimer, the term of this patent is extended or adjusted under 35 U.S.C. 154(b) by 0 days.

(21) Appl. No.: 09/593,359

(22) Filed: Jun. 14, 2000

(51) Int. Cl.⁷ .............................. A01H 1/00; A01H 5/00; C07H 21/04; C12N 5/04; C12N 15/82

(52) U.S. Cl. ....................... 800/281; 800/298; 435/419; 435/468; 536/23.6

(58) Field of Search ................................. 800/290, 298, 800/281; 435/419, 440, 468, 69.1; 536/23.1, 23.6; 530/372

(56) References Cited

U.S. PATENT DOCUMENTS

| | | | |
|---|---|---|---|
| 4,407,956 A | 10/1983 | Howell et al. | 435/172 |
| 4,666,844 A | 5/1987 | Cheng et al. | 435/240 |
| 5,589,617 A | 12/1996 | Nehra et al. | 800/205 |
| 5,631,152 A | 5/1997 | Fry et al. | 435/172.3 |
| 5,874,265 A | 2/1999 | Adams et al. | 435/172.3 |

FOREIGN PATENT DOCUMENTS

| | | | | |
|---|---|---|---|---|
| WO | WO 98/55631 | 12/1998 | | C12N/15/54 |
| WO | WO99/67268 | 12/1999 | | C07H/21/04 |
| WO | WO 99/67368 | 12/1999 | | C12N/9/10 |
| WO | WO 99/67403 | 12/1999 | | C12N/15/82 |
| WO | WO 00/01713 | 1/2000 | | |

OTHER PUBLICATIONS

Burgess et al., Possible Dissociation of the Heparin–binding and Mitogenic Activities of Heparin–binding (Acidic Fibroblast) Growth Factor–1 . . . , 1990, The Jornal of Cell Biology, vol. 111, pp. 2129–2138.*
Bowie et al., Deciphering the Message in Protein Sequences: Tolerance to Amino Acid Substitutions, Mar. 16, 1990, Science, vol. 247, pp. 1306–1310.*
Hobbs et al., Cloning of cDNA encoding diaclyglycerol acyltransferase from Arabidopsis thalaiana and its functional expression, 1999, FEBS Letter, vol. 452, pp. 145–149.*
Frentze, Acyltansferases from basic science to modified seed oils, 1998, pp. 161–166.*
Wiberg et al., Substrates of Diacylglycerol Acyltransferase in Microsomes from Developing Oil Seeds, 1994, Phytochemistry, vol. 36, No. 3, pp. 573–577.*
Moloney, M.M., Walker, J.M. and Sharma, K.K. (1989) High efficiency transformation of Brassica napus using Agrobacterium vectors. Plant Cell Reports 8:238–242.

Oo, K–C. and Chew, Y–H. (1992) Diacylglycerol acyltransferase in microsomes and oil bodies of oil palm mesocarp. Plant Cell Physiology 33:189–195.
Orr, W., Keller, W.A. and Singh, J. (1986) Induction of freezing tolerance in an embryogenic cell suspension culture of Brassica napus by abscisic acid at room temperature. Journal of Plant Physiology 126:23–32.
Parrott, W. A., Merkel, S. A. and Williams, E. G. (1991) Somatic embryogenesis: Potential for use in propagation and gene transfer systems. In: Advanced Methods in Plant Breeding and Biotechnology, Murray D.R. (Ed.), CAB International, Wallingford, pp. 158–200.
Perry, H.J. and Harwood, J.L. (1993) Changes in the lipid content of developing seeds of Brassica napus. Phytochemistry 32:1411–1415.
Ritala, A., Aspegren, K, Kurtén, U., Salmenkallio–Marttila, M., Mannonen, L., Hannus, R., Kauppinen, V., Teeri, T. H. and Enari, T.–M. (1994) Fertile transgenic barley by particle bombardment of immature embryos. Plant Molecular Biology 24:317–325.
Rosenberg, I.M. (1996) Protein Analysis and Purification. Benchtop Techniques. Birkhauser, Berlin.
Routaboul, J., Benning, C., Bechtold, N., Caboche, M., Lepiniec, L. (1999) The TAG1 locus of Arabidospis encodes for a diacylglycerol acyltransferase. Plant Physiol. Biochem. 37(11):831–840.
Sambrook, J., Fritsch, E.F. and Maniatis. T. (1989) Molecular Cloning: A Laboratory Manual. Second ed. Cold Spring Harbor Press, New York.
Scofield, S.R. and Crouch, M.L. (1987) Nucleotide sequence of a member of the napin storage protein family from Brassica napus. The Journal of Biological Chemistry 262:12202–12208.
Settlage, S.B., Kwanyuen, P. and Wilson, R.F. (1998) Relation between diacylglycerol acyltransferase activity and oil concentration in soybean, Journal of American Oil Chemists Society 75: 775–781.
Stalker, D.M., Thomas, C.M. and Helinski, D.R. (1981) Nucleotide sequence of the region of the origin of replication of the broad host range plasmid RK2. Molecular and General Genetics 181:8–12.
Steinecke, P., Herget, T. and Schreier, P.H. (1992) Expression of a chimeric ribozyme gene results in endonucleolytic cleavage of target mRNA and a concomitant reduction of gene expression in vivo. The EMBO Journal. 11:1525–1530.

(List continued on next page.)

Primary Examiner—Elizabeth F. McElwain
Assistant Examiner—Stuart Baum
(74) Attorney, Agent, or Firm—Greenlee Winner and Sullivan, P.C.

(57) ABSTRACT

Isolated polynucleotides encoding Brassica napus diacylglycerol O-acyltransferase (DGAT) are provided. Also provided are the encoded DGAT polypeptides, transgenic plants which express DGAT, and methods for making such plants. The DGAT-encoding polynucleotides are useful for increasing triacylglycerol (TAG) synthesis, seed oil content, and oil quality in plants.

27 Claims, 1 Drawing Sheet

OTHER PUBLICATIONS

Stone, Sophia L.., Amoldo, M.A. and Goring, D.R. (1999) A breakdown of Brassica self–incompatibility in ARC1 antisense transgenic plants. Science 286:1729–1731.

Alber, T. and Kawasaki, G. (1982) Nucleotide sequence of the triose phosphate isomerase gene of *Saccharomyces cerevisiae.* Journal of Molecular and Applied Genetics 1: 419–434.

Altschul, Stephen F., et al. (1990) Basic Local Alignment Search Tool. Journal of Molecular Biology. 215:403–410.

Altschul, Stephen, F., et al. (1997) Gapped BLAST and PSI–BLAST: a new generation of protein database search programs. Nucleic Acids Research 25:3389–3402.

Ausubel, F.M., et al. (2000) Current Protocols in Molecular Biology. John Wiley & Sons, New York.

Beetham, P. R., et al. (1999) A tool for functional plant genomics: Chimeric RNA/DNA oligonucleotides cause in vivo gene–specific mutations. Proc. Natl. Acad. Sci. U.S.A. 96:8774–8778.

Bevan, M.W., Flavell R.B. and Chilton, M.D. (1983) A chimaeric antibiotic resistance gene as a selectable marker for plant cell transformation. Nature (London) 304:184–187.

Bevan, M., et al. (1986) The structure and transcription start site of a major potato tuber protein gene. Nucleic Acids Research 14:4625–4683.

Bommineni, V.R., Jauhar, P.P. and Peterson, T.S. (1997) Transgenic durum wheat by microprojectile bombardment of isolated scutella. Journal of Heredity. 88:475–481.

Bouvier–Nave, P., et al. (2000) Expression in yeast and tobacco of plant cDNAs encoding acyl CoA:diacylglyerol acyltransferase. Eur. J. Biochem. 267:85–96.

Bradford, M. (1976) A rapid and sensitive method for the quantitation of microgram amounts of protein using the principle of protein–dye binding. Analytical Biochmistry 72:248–254.

Breen, J.P. and Crouch, M.L. (1992) Molecular analysis of a Cruciferin storage protein gene family of *Brassica napus.* Plant Molecular Biology 19: 1049–1055.

Browse J., McCourt P.J. and Somerville, C.R. (1986) Fatty acid composition of leaf lipids determined after combined digestion and fatty acid methyl ester formation from fresh tissue. Analytical Biochemistry 152: 141–145.

Cases, S., et al. (1998) Identification of a gene encoding an acyl CoA:diacylglycerol acyltransferase, a key enzyme in triacylglycerol synthesis. Proceedings of the National Academy of Sciences USA 95:13018–13023.

Cho, M.–J., Jiang, W. and Lemaux, P.G. (1998) Transformation of recalcitrant barley cultivars through improvement of regenerability and decreased albinism. Plant Science 138:229–244.

Christie, W. (1992) Preparation of fatty acid methyl esters. INFORM 3: 1031–1034.

De Block, M. (1988) Genotype–independent leaf disc transformation of potato (*Solanum tuberosum*) using *Agrobacterium tumefaciens.* Theoretical and Applied Genetics 76:767–774.

Depicker, A., Stachel, S., Dhaese, P., Zambryski, P. and Goodman, H.M. (1982) Nopaline synthease: transcript mapping and DNA sequence *Agrobacterium tumefaciens.* Journal of Molecular and Applied Genetics 1: 561–573.

Deutscher, M.P. (1990) Guide to Protein Purification. Methods in Enzymology vol. 812. Academic Press, New York.

Erickson, F.L., Holzber, S., Calderon–Urrea, A., Handley, V., Axtell, M., Corr, C. and Baker, B. 1999. The helicase domain of the TMV replicase proteins induces the N–mediated defence response in tobacco. The Plant Journal 18: 67–75.

Fling, M.E., Kopf, I. and Richards, C. (1985) Nucleotide sequence of the rtransposon Tn7 gene encoding an aminoglucoside–modifiying enzyme 3"(9)–O–nucleotidyltransferase. Nucleic Acids Research 13: 7095–7106.

Fraley, R.T., Rogers, S.G., Horsch, R.B., Sanders, P.R., and Flick, J.S. (1983) Expression of bacterial genes in plant cells *Agrobacterium tumefaciens.* Proceedings of the National Academy of Sciences USA 80:4803–4807.

Fraley, R.T., Rogers, S.G., Horsch, R.B., Eichholtz, D.A.. Flick, J.S, C.L., Hoffmann, N.L., and Sanders, P.R. (1985) The SEV system: a new disarmed Ti plasmid vector system for plant transformation. Bio/Technology 3:629–635.

Frentzen, M. (1993) Acyltransferases and triacylglycerols. In: Moore Jr., T.S. ed., Lipid metabolism in plants. Ann Arbor:CRC Press. pp. 195–230.

Frohman, M.A. (1995) Rapid amplification of cDNA ends. In PCR Primer A Laboratory Manual. Dieffenbach, C.W. and Dveskler G.S. eds. Cold Spring Harbor Laboratory Press, New York, pp. 381–409.

GenBank Accession No. AF051849 (Jan. 24, 2000) *Arabidopsis thaliana* diacylglycerol acyltransferase (DAGAT) mRNA, complete cds.

GenBank Accession No. AF078752 (Nov. 11, 1998) Mus musculus diacylglycerol acyltransferase (Dgat) mRNA, complete cds.

GenBank Accession No. AF155224 (Aug. 25, 1999) *Brassica napus* putative diacylglycerol acyltransferase (DGAT2) mRNA, complete cds.

GenBank Accession No. AF164434 (Nov. 30, 1999) *Brassica napus* dacylglycerol acyltransferase (DGAT1) mRNA, complete cds.

GenBank Accession No. AF251794 (Apr. 16, 2000) *Brassica napus* putative diacylglycerol acyltransferase mRNA.

GenBank Accession No. AJ131831 (Jun. 10, 1999) *Arabidopsis thaliana* mRNA for diacylglycerol O–transferase.

GenBank Accession No. AJ238008 (Jun. 18, 1999) *Arabidopsis thaliana* mRNA for dacylglycerol acyltransferase.

GenBank Accession No. AW702139 (Apr. 18, 2000) uq98d11.x1 NC_CGAP_Mam10 Mus musculus cDNA clone Image:2939157 3' similar to TR:Q9Z2A7 Q9Z2A7 Diacylglycerol acyltransferase.; mRNA sequence.

GenBank Accession No. AW742050 (Apr. 27, 2000) uq98d11.y1 NC_CGAP_Mam10 Mus musculus cDNA clone Image:2939157 3' similar to TR:Q9Z2A7 Q9Z2A7 Diacylglycerol acyltransferase.; mRNA sequence.

GenBank Accession No. AC003058 (Apr. 5, 2000) *Arabidopsis thaliana* chromosome II section 112 of 255 of the complete sequence. Sequence from clones T20K24, F27F23.

GenBank Accession No. AC005917 (Apr. 5, 2000) *Arabidopsis thaliana* chromosome II section 113 of 255 of the complete sequence. Sequence from clones F27F23, F3P11.

Gielen, J., De Beuckeleer, M., Seurinck, J., Deboeck, F., and De Greve, H. (1984) The complete nucleotide sequence of the TL–DNA of the *Agrobacterium tumefaciens* plasmid pTiAch5. EMBO Journal 3: 835–846.

Gelvin, S.B., Schilperoort, R.A. and Verma, D.P.S. (1994) Plant Molecular Biology Manual. Kluwer Academic Publishers. Belgium.

Gerhardt, P., Murray, R.G.E., Wood, W.A. and Krieg, N.R. (1994). Methods for General and Molecular Bacteriology. American Society for Microbiology. Washington, D.C., USA.

Hajdukiewicz, P., Svab, Z. and Maliga, P. (1994) The small, versatile pPZP family of Agrobacterium binary vectors for plant transformation. Plant Molecular Biology 25: 989–994.

Hara, A. and Radin, M.S. 1978. Lipid extraction of tissues with a low toxicity solvent. Analatycal Biochemistry 90:420–426.

Harris, E.L.V. and Angal, S. (1989) Protein purification methods a practical approach. IRL Press, New York.

Henzi, M.X., Christey, M.C., McNeil, D.L. and Davies, K.M. (1999) Agrobacterium rhizogenes–mediated transformation of broccoli (Brassica oleracea L. var. italics) with an antisense 1–aminocyclopropane–1–carboxyicacid oxidase gene. Plant Science 143:55–62.

Henikoff, S. and Henikoff, J.G. (1992) Amino acid substitution matrices from protein blocks. Proceedings of the National Academy of Sciences USA 89: 10915–10919.

Hobbs, D.J., Lu, C. and Hills, M. (1999) Cloning of a cDNA encoding diacylglycerol acyltransferase from Arabidopsis thaliana and its functional expression. FEBS Letters. 452:145–149.

Ichihara, K., Takahashi, T. and Fujii, S. (1988) Diacylglycerol acyltransferase in maturing safflower seeds: its influence on the fatty acid composition of triacylglycerol and on the rate of triacylglycerol synthesis. Biochimica et Biophysica Acta 958:125–129.

Janson, J–C. and Ryden, L. (1998) Protein Purification. Principles, High–resolution Methods, and Applications. Wiley–Liss, New York.

Kamisaka, Y., Mishra, S. and Nakahara, T. (1997) Purification and characterization of diacylglycerol acyltransferase from the lipid body fraction of an oleaginous fungus. Journal Biochemistry 121:1107–1114.

Kay, R., Chan, A., Daly, M. and McPherson, J. (1987) Duplication of CaMV 35S promoter sequences creates a strong enhancer for plant genes. Science 236: 1299–1302.

Kemper, E.L., da Silva, M.J. and Arruda, P. (1996) Effect of microprojectile bombardment parameters and osmotic treatment on particle penetration and tissue damage in transiently transformed cultured immature maize (Zea mays L.) embryos. Plant Science 121:85–93.

Lin, X., et al. (1999) Sequence and analysis of chromosome 2 of the plant Arabidopsis thaliana. Nature 402:761–768.

Little, D., Weselake, R., Pomeroy, K., Furukawa–Stoffer T. and Bagu, J. (1994) Solubilization and characterization of diacylglycerol acyltransferase from microspore–derived cultures of oilseed rape. Biochemical Journal 304:951–958.

Lörz, H., Becker, D. and Lütticke, S. (1998) Molecular wheat breeding by direct gene transfer. Euphytica 100: 219–223.

McElroy, D., Blowers, A.D., Jenes, B. and Wu, R. (1991) Construction of expression vectors based on the rice actin 1 (Act1) 5'region for use in monocot transformation. Molecular and General Genetics 231:150–160.

Moloney, M.M., Walker, J.M. and Sharma, K.K. (1989) High efficiency transformation of Brassica napus using Agrobacterium vectors. Plant Cell Reports 8:238–242.

Nehra, N.S., Chibbar, R.N., Leung, N., Caswell, K., Mallard, C., Steinhauer, L., Baga M. and Kartha, K.K. (1994) Self–fertile transgenic wheat plants regenerated from isolated scutellar tissues following microprojectile bombardment with two distinct gene constructs. The Plant Journal 5:285–297.

Nykiforuk, C.L., Laroche, A., Weselake, R. (1999) Isolation and sequence analysis of a novel cDNA encoding a putative diacylglycerol acyltransferase from a microspore–derived cell suspension culture of Brassica napus L. cv Jet Neuf (Accession No. aF155224). Plant Physiology. 120:1207.

Nykiforuk, C.L., Laroche, A., Weselake, R. (1999) Isolation and characterization of a cDNA encoding a second putative diacylglycerol acyltransferase from a microspore–derived cell suspension culture of Brassica napus L. cv Jet Neuf (Accession No. AF164434). Plant Physiology. 121:1057.

Odell, J.T., Nagy, F. and Chua, N.–H. (1985) Identification of DNA sequences required for activity of the cauliflower mosaic virus 35S promoter. Nature 313:810–812.

Oo, K–C. and Chew, Y–H. (1992) Diacylglycerol acyltransferase in microsomes and oil bodies of oil palm mesocarp. Plant Cell Physiology 33:189–195.

Orr, W., Keller, W.A. and Singh, J. (1986) Induction of freezing tolerance in an embryogenic cell suspension culture of Brassi napus by abscisic acid at room temperature. Journal of Plant Physiology 126:23–32.

Parrott, W. A., Merkle, S. A. and Williams, E. G. (1991) Somatic embryogenesis: Potential for use in propagation and gene transfer systems. In: Advanced Methods in Plant Breeding snd Biotechnology, Murray D.R. (Ed.), CAB International, Wallingford, pp. 158–200.

Perry, H.J. and Harwood, J.L. (1993) Changes in the lipid content of developing seeds of Brassica napus. Phytochemistry 32:1411–1415.

Ritala, A., Aspergren, K., Kurtén, U., Salmenkallio–Marttila, M., Mannonen, L., Hannus, R., Kauppinen, V., Teeri, T. H. and Enari, T.–M. (1994) Fertile transgenic barley by particle bombardment of immature embryos. Plant Molecular Biology 24:317–325.

Rosenberg, I.M. (1996) Protein Analysis and Purification. Benchtop Techniques. Birkhauser, Berlin.

Routaboul, J., Benning, C., Bechtold, N., Caboche, M., Lepiniec. L. (1999) The TAG1 locus of Arabidopsis encodes for a diacylglycerol acyltransferase. Plant Physiol. Biochem. 37(11):831–840.

Sambrook, J., Fritsch, E.G. and Maniatis, T. (1989) Molecular Cloning: A Laboratory Manual. Second ed. Cold Spring Harbor Press, New York.

Scofield, S.R. and Crouch, M.L. (1987) Nucleotide sequence of a member of the napin storage protein family from Brassica napus. The Journal of Biological Chemistry.

Settlage, S.B., Kwanyuen, P. and Wilson, R.F. (1998) Relation between diacylglycerol acyltransferase activity and oil concentration in soybean. Journal of American Oil Chemists Society 75: 775–781.

Stalker, D.M., Thomas, C.M. and Helinski, D.R. (1981) Nucleotide sequence of the region of the origin of replication of the broad host range plasmid RK2, Molecular and General Genetics 181:81–2.

Steinecke, P., Herget, T. and Schreier, P.H. (1992) Expression of a chimeric ribozyme gene results in endonucleolytic cleavage of target mRNA and a concomitant reduction of gene expression in vivo. The EMBO Journal. 11:1525–1530.

Stone, Sophia L., Arnoldo, M.A. and Goring, D.R. (1999) A breakdown of Brassica self–incompatibility in ARC1 antisense transgenic plants. Science 286:1729–1731.

Stymne, S. and Stobart, A.K. (1987) Triacylglycerol biosynthesis. In The Biochemistry of Plants, Vol. 9. Lipids: Structure and Function. Stumpf. P.K. ed., Academic Press, New York, pp. 175–214.

Takumi, S. and Shimada, T. (1997) Variation in transformation frequencies among six common wheat cultivars through particle bombardment of scutellar tissues. Genes Genet. Syst. 72: 63–69.

Tingay, S., McElroy, D., Kalla, R., Fieg, S., Wang, M., Thornton, S., and Brettell, R. (1997) *Agrobacterium tumefaciens*–mediated barley transformation. The Plant Journal 11: 1369–1376.

Trick, H.M. and Finer, J. J. (1997) SAAT: sonication–assisted Agrobacterium–mediated transformation. Transgenic Research 6: 329–336.

van Rooijen, G.J.H. and Moloney, M.M. (1994) Plant seed oil–bodies as carriers for foreign proteins. Bio/Technology 13:72–77.

Wan, Y. and Lemaux, P.G. (1994) Generation of large numbers of independently transformed fertile barley plants. Plant Physiology 104: 37–48.

Weeks, J.T., Anderson, O.D. and Blechl, A.E. (1993) Rapid production of multiple independent lines of fertile transgenic wheat (*Triticum aestivum*). Plant Physiol. 102:1077–1084.

Wegener, D., Steinecke, P., Herget, T., Petereit, I., Philipp, C. and Schreier, P.H. (1994) expression of a reporter gene is reduced by a ribozyme in transgenic plants. Molecular and Genreal Genetics 245: 465–470.

Weselake, R.J., et al. (1998) Triacylglycerol biosynthesis and gene expression in microspore–derived cell suspension cultures of oilseed rape. Journal of Experimental Botany 49: 33–39.

Weselake, R.J. and Taylor, D.C. (1999) The study of storage lipid biosynthesis using microspore–derived cultures of oilseed rape. Progress in Lipid Research 38:401–460.

White, J., Chang, S.Y., Bibb, M.J. and Bibb, M.J. (1990) A cassette containing the bar gene of *Streptomyces hygroscopious:* a selectable marker for plant transformation. Nucleic Acids Research 18:1062.

Yao, Q.A., Simion, E., William, M., Krochko, J. and Kasha, K.J. (1997) Biolistic transformation of haploid isolated microspores of barley (*Hordium vulgare*L.). Genome 40:570–581.

Zhu, T., Peterson, D.J., Tagliani, L., St. Clair, G., Baszcynski, C.L. and Bowen, B. (1999) Targeted manipulation of maize genes in vivo using chimeric RNA/DNA oligonucleotides. Proceedings of the National Academy of Science U.S.A 96 8768–8773.

Zou, J., Wei Y., Jake, C., Kumar A., Selvaraj G., and Taylor D.C. (1999) The Arabidopsis thaliana TAG1 mutant has a mutation in a diacylglycerol acyltransferase gene. The Plant Journal 19(6):645–653.

* cited by examiner

```
163 MCCLSLSVFPLAAFTVEKMVLQKFISEPVAIILHVIITMTEVLYPVYVTL 212
    ||||||:|||||||||||:||||  |||||  |  |||||||||||||||
  1 MCCLSLSIFPLAAFTVEKLVLQKCISEPVVIFLHVIITMTEVLYPVYVTL 50

213 RCDSAFLSGVTLMLLTCIVWLKLVSYAHTSYDIRTLANSADKVDPEISYY 262
    ||||||||| |||||||||||||||||| ||||||||||| || ||:|||
 51 RCDSAFLSGDTLMLLTCIVWLKLVSYAHTNYDIRTLANSSDKANPEVSYY 100

263 VSLKSLAYFMVAPTLCYQPSYPRSPCIRKGWVARQLAKLVIFTGLMGFII 312
    |||||||||| ||||||||||||||||||||||||| ||||||||||||||
101 VSLKSLAYFMLAPTLCYQPSYPRSPCIRKGWVARQFAKLVIFTGLMGFII 150

313 EQYINPIVRNSKHPLKGDLLYAIERVLKLSVPNLYVWLCMFYCFFHLWLN 362
    |||||||||||||||||||||||||||||||||||||||||||||||||
151 EQYINPIVRNSKHPLKGDLLYAIERVLKLSVPNLYVWLCMFYCFFHLWLN 200

363 ILAELLCFGDREFYKDWWNAKSVGDYWRMWNMPVHKWMVRHVYFPCLRIK 412
    |||||||||||||||||||||||||||||||||||||||||||||||||
201 ILAELLCFGDREFYKDWWNAKSVGDYWRMWNMPVHKWMVRHVYFPCLRIK 250

413 IPKVPAIIIAFLVSAVFHELCIAVPCRLFNLWAFMGIMFQVPLVFITNFL 462
    |||||||||||||||||||||||||||||||||||||||||||||||||
251 IPKVPAIIIAFLVSAVFHELCIAVPCRLFNLWAFMGIMFQVPLVFITNFL 300

463 QERFGSMVGNMIFGSASCIFGQPMCGLLYYHDLMNRKGSMS 503
    ||||||||||||||||||||||||||||||||||||||||
301 QERFGSMVGNMIFGSASCIFGQPMCGLLYYHDLMNRKGSMS 341
```

FIG. 1

SEQUENCE LISTING

```
<160> NUMBER OF SEQ ID NOS: 17

<210> SEQ ID NO 1
<211> LENGTH: 1446
<212> TYPE: DNA
<213> ORGANISM: Brassica napus
<220> FEATURE:
<223> OTHER INFORMATION: DGAT2
<221> NAME/KEY: CDS
<222> LOCATION: (82)..(1107)

<400> SEQUENCE: 1
cgaaaatctc atgaagtacg gttggttgat cagaactgat ttctggttta gttcaacgtc      60
gctgcgagat tgccgctttt c atg tgt tgt ctc tcc ctt tca atc ttt cct      111
                        Met Cys Cys Leu Ser Leu Ser Ile Phe Pro
                         1               5                      10 ttg gct gcc ttt acc gtc gag aaa tta gta ctt cag aaa tgc ata tct      159
Leu Ala Ala Phe Thr Val Glu Lys Leu Val Leu Gln Lys Cys Ile Ser
             15                  20                  25 gaa cct gtt gtc atc ttt ctt cat gtt att atc acc atg acc gag gtc      207
Glu Pro Val Val Ile Phe Leu His Val Ile Ile Thr Met Thr Glu Val
         30                  35                  40 ttg tat cca gtc tat gtc act cta agg tgt gat tct gcc ttc tta tca      255
Leu Tyr Pro Val Tyr Val Thr Leu Arg Cys Asp Ser Ala Phe Leu Ser
     45                  50                  55 ggt gac acg ttg atg ctc ctc act tgc att gtg tgg ctg aag ttg gtt      303
Gly Asp Thr Leu Met Leu Leu Thr Cys Ile Val Trp Leu Lys Leu Val
 60                  65                  70 tct tac gct cat act aac tat gac ata aga acc cta gct aat tca tct      351
Ser Tyr Ala His Thr Asn Tyr Asp Ile Arg Thr Leu Ala Asn Ser Ser
 75                  80                  85                  90 gat aag gcc aat cct gaa gtc tcc tac tat gtt agc ttg aag agc ttg      399
Asp Lys Ala Asn Pro Glu Val Ser Tyr Tyr Val Ser Leu Lys Ser Leu
                 95                 100                 105 gct tat ttc atg ctt gct ccc aca ttg tgt tat cag cca agc tat cca      447
Ala Tyr Phe Met Leu Ala Pro Thr Leu Cys Tyr Gln Pro Ser Tyr Pro
             110                 115                 120 cgt tct cca tgt atc cgg aag ggt tgg gtg gct cgt caa ttt gca aaa      495
Arg Ser Pro Cys Ile Arg Lys Gly Trp Val Ala Arg Gln Phe Ala Lys
         125                 130                 135 ctg gtc ata ttc act gga ctc atg gga ttt ata ata gag caa tat ata      543
Leu Val Ile Phe Thr Gly Leu Met Gly Phe Ile Ile Glu Gln Tyr Ile
     140                 145                 150
```

```
aat cct att gtt agg aac tca aag cat cct ctg aaa ggg gac ctt cta      591
Asn Pro Ile Val Arg Asn Ser Lys His Pro Leu Lys Gly Asp Leu Leu
155                 160                 165                 170 tat gct att gaa aga gtg ttg aag ctt tca gtt cca aat cta tat gtg      639
Tyr Ala Ile Glu Arg Val Leu Lys Leu Ser Val Pro Asn Leu Tyr Val
                175                 180                 185 tgg ctc tgc atg ttc tac tgc ttc ttc cac ctt tgg tta aac ata ttg      687
Trp Leu Cys Met Phe Tyr Cys Phe Phe His Leu Trp Leu Asn Ile Leu
            190                 195                 200 gca gag ctc ctc tgc ttc ggg gac cgt gaa ttc tac aaa gat tgg tgg      735
Ala Glu Leu Leu Cys Phe Gly Asp Arg Glu Phe Tyr Lys Asp Trp Trp
        205                 210                 215 aat gca aaa agc gtt gga gat tat tgg aga atg tgg aat atg cct gtt      783
Asn Ala Lys Ser Val Gly Asp Tyr Trp Arg Met Trp Asn Met Pro Val
    220                 225                 230 cac aaa tgg atg gtt cga cat gta tac ttt ccg tgc ctg cgc atc aag      831
His Lys Trp Met Val Arg His Val Tyr Phe Pro Cys Leu Arg Ile Lys
235                 240                 245                 250 ata cca aaa gta ccc gcc att atc att gct ttc tta gtc tct gca gtc      879
Ile Pro Lys Val Pro Ala Ile Ile Ile Ala Phe Leu Val Ser Ala Val
                255                 260                 265 ttt cat gag tta tgc atc gca gtt cct tgc cgt ctc ttc aat cta tgg      927
Phe His Glu Leu Cys Ile Ala Val Pro Cys Arg Leu Phe Asn Leu Trp
            270                 275                 280 gct ttc atg gga att atg ttt cag gtc cct ttg gtc ttt atc aca aac      975
Ala Phe Met Gly Ile Met Phe Gln Val Pro Leu Val Phe Ile Thr Asn
        285                 290                 295 ttt tta caa gaa agg ttt ggc tcc atg gtg gga aac atg atc ttt ggt     1023
Phe Leu Gln Glu Arg Phe Gly Ser Met Val Gly Asn Met Ile Phe Gly
    300                 305                 310 tca gct tct tgc att ttc gga caa ccg atg tgt ggg ctt ctt tat tac     1071
Ser Ala Ser Cys Ile Phe Gly Gln Pro Met Cys Gly Leu Leu Tyr Tyr
315                 320                 325                 330 cat gac ctg atg aac cgc aaa gga tcc atg tcc tga aaaggacttt         1117
His Asp Leu Met Asn Arg Lys Gly Ser Met Ser
                335                 340 ttacgcccca aaaaaaaaat tggtcaattg gaaaatgggg agttttttgta tccttttggt  1177 agccgttaaa atgcctttaa aaagacgaat cctttggagt tcttgtttct cttggtctct  1237
gtcccccacg ggattttcta tttctcgtct tttaacaagc ccataaaaaa aagtagactg  1297
agataattgg attttgttat gctgtaaaaa aaatttcatt caaaaatgtt tgaataatct  1357
ttgacgattc ccaaaatccc gagaaaaata aagtaagcc tttccttttt aaaaaaaaaa   1417
aaaaaaaaaa aaaaaaaaaa aaaaaaaaa                                    1446

<210> SEQ ID NO 2
<211> LENGTH: 341
<212> TYPE: PRT
<213> ORGANISM: Brassica napus
<223> OTHER INFORMATION: DGAT2

<400> SEQUENCE: 2

Met Cys Cys Leu Ser Leu Ser Ile Phe Pro Leu Ala Ala Phe Thr Val
 1               5                  10                  15

Glu Lys Leu Val Leu Gln Lys Cys Ile Ser Glu Pro Val Val Ile Phe
            20                  25                  30

Leu His Val Ile Ile Thr Met Thr Glu Val Leu Tyr Pro Val Tyr Val
        35                  40                  45

Thr Leu Arg Cys Asp Ser Ala Phe Leu Ser Gly Asp Thr Leu Met Leu
```

```
                50                      55                      60
Leu Thr Cys Ile Val Trp Leu Lys Leu Val Ser Tyr Ala His Thr Asn
 65                      70                      75                      80

Tyr Asp Ile Arg Thr Leu Ala Asn Ser Ser Asp Lys Ala Asn Pro Glu
                 85                      90                      95

Val Ser Tyr Tyr Val Ser Leu Lys Ser Leu Ala Tyr Phe Met Leu Ala
                100                     105                     110

Pro Thr Leu Cys Tyr Gln Pro Ser Tyr Pro Arg Ser Pro Cys Ile Arg
                115                     120                     125

Lys Gly Trp Val Ala Arg Gln Phe Ala Lys Leu Val Ile Phe Thr Gly
                130                     135                     140

Leu Met Gly Phe Ile Ile Glu Gln Tyr Ile Asn Pro Ile Val Arg Asn
145                     150                     155                     160

Ser Lys His Pro Leu Lys Gly Asp Leu Leu Tyr Ala Ile Glu Arg Val
                165                     170                     175

Leu Lys Leu Ser Val Pro Asn Leu Tyr Val Trp Leu Cys Met Phe Tyr
                180                     185                     190

Cys Phe Phe His Leu Trp Leu Asn Ile Leu Ala Glu Leu Leu Cys Phe
                195                     200                     205

Gly Asp Arg Glu Phe Tyr Lys Asp Trp Trp Asn Ala Lys Ser Val Gly
                210                     215                     220

Asp Tyr Trp Arg Met Trp Asn Met Pro Val His Lys Trp Met Val Arg
225                     230                     235                     240

His Val Tyr Phe Pro Cys Leu Arg Ile Lys Ile Pro Lys Val Pro Ala
                245                     250                     255

Ile Ile Ile Ala Phe Leu Val Ser Ala Val Phe His Glu Leu Cys Ile
                260                     265                     270

Ala Val Pro Cys Arg Leu Phe Asn Leu Trp Ala Phe Met Gly Ile Met
                275                     280                     285

Phe Gln Val Pro Leu Val Phe Ile Thr Asn Phe Leu Gln Glu Arg Phe
290                     295                     300

Gly Ser Met Val Gly Asn Met Ile Phe Gly Ser Ala Ser Cys Ile Phe
305                     310                     315                     320

Gly Gln Pro Met Cys Gly Leu Leu Tyr Tyr His Asp Leu Met Asn Arg
                325                     330                     335

Lys Gly Ser Met Ser
            340

<210> SEQ ID NO 3
<211> LENGTH: 1512
<212> TYPE: DNA
<213> ORGANISM: Brassica napus
<220> FEATURE:
<223> OTHER INFORMATION: DGAT1
<221> NAME/KEY: CDS
<222> LOCATION: (1)..(1512)

<400> SEQUENCE: 3 atg gcg att ttg gat tct gga ggc gtc gct gta ccg ccg acg gag aac      48
Met Ala Ile Leu Asp Ser Gly Gly Val Ala Val Pro Pro Thr Glu Asn
 1               5                  10                  15 ggc gtc gcg gat ctc gac agg ctc cac cgt cgt aaa tcg agt tcg gat      96
Gly Val Ala Asp Leu Asp Arg Leu His Arg Arg Lys Ser Ser Ser Asp
             20                  25                  30 tct tcc aac gga ctc ctc tcc gat act tcc ccg tcg gac gat gtt gga     144
Ser Ser Asn Gly Leu Leu Ser Asp Thr Ser Pro Ser Asp Asp Val Gly
         35                  40                  45
```

```
gct gcg gcg gcc gaa agg gat cgg gtt gat tcc gct gcc gag gag gag    192
Ala Ala Ala Ala Glu Arg Asp Arg Val Asp Ser Ala Ala Glu Glu Glu
     50                  55                  60 gct cag gga aca gcg aat tta gct ggc gga gat gcc gaa act agg gaa    240
Ala Gln Gly Thr Ala Asn Leu Ala Gly Gly Asp Ala Glu Thr Arg Glu
 65                  70                  75                  80 tcc gcc gga ggc gat gta agg ttt acg tat cga ccg tcg gtt cca gct    288
Ser Ala Gly Gly Asp Val Arg Phe Thr Tyr Arg Pro Ser Val Pro Ala
                 85                  90                  95 cat cgg agg acg agg gag agt cct ctc agc tcc gac gct atc ttc aaa    336
His Arg Arg Thr Arg Glu Ser Pro Leu Ser Ser Asp Ala Ile Phe Lys
            100                 105                 110 caa agc cat gca gga ttg ttc aac ctc tgt gta gtt gtt ctt gtt gct    384
Gln Ser His Ala Gly Leu Phe Asn Leu Cys Val Val Val Leu Val Ala
        115                 120                 125 gtt aac agt aga ctc atc atc gaa aac ctc atg aag tat ggt tgg ttg    432
Val Asn Ser Arg Leu Ile Ile Glu Asn Leu Met Lys Tyr Gly Trp Leu
    130                 135                 140 atc aga act gat ttt tgg ttt agt tct aca tcc tta cga gac tgg ccg    480
Ile Arg Thr Asp Phe Trp Phe Ser Ser Thr Ser Leu Arg Asp Trp Pro
145                 150                 155                 160 ctt ttc atg tgt tgt ctt tca ctt tcg gtc ttt cct ttg gct gcc ttc    528
Leu Phe Met Cys Cys Leu Ser Leu Ser Val Phe Pro Leu Ala Ala Phe
                165                 170                 175 acg gtc gag aaa atg gta ctt cag aaa ttc ata tct gag cct gtt gcc    576
Thr Val Glu Lys Met Val Leu Gln Lys Phe Ile Ser Glu Pro Val Ala
            180                 185                 190 atc att ctt cat gtc att ata acc atg aca gag gtc ttg tat cca gtc    624
Ile Ile Leu His Val Ile Ile Thr Met Thr Glu Val Leu Tyr Pro Val
        195                 200                 205 tac gtc aca ctg agg tgt gat tct gcc ttc ttg tca ggt gtc acg ttg    672
Tyr Val Thr Leu Arg Cys Asp Ser Ala Phe Leu Ser Gly Val Thr Leu
    210                 215                 220 atg ctg ctc act tgc att gtg tgg ctg aag ttg gtt tct tac gct cat    720
Met Leu Leu Thr Cys Ile Val Trp Leu Lys Leu Val Ser Tyr Ala His
225                 230                 235                 240 act agc tac gac ata aga acc ctg gcc aat tca gct gat aag gtc gat    768
Thr Ser Tyr Asp Ile Arg Thr Leu Ala Asn Ser Ala Asp Lys Val Asp
                245                 250                 255 cct gaa atc tcc tac tat gtt agc ttg aag agc ttg gcg tat ttc atg    816
Pro Glu Ile Ser Tyr Tyr Val Ser Leu Lys Ser Leu Ala Tyr Phe Met
            260                 265                 270 gtt gct ccc aca ctg tgt tat cag cca agc tat cca cgt tct cca tgt    864
Val Ala Pro Thr Leu Cys Tyr Gln Pro Ser Tyr Pro Arg Ser Pro Cys
        275                 280                 285 atc cgg aag ggt tgg gtg gct cgt caa ctt gca aaa ctg gtc ata ttc    912
Ile Arg Lys Gly Trp Val Ala Arg Gln Leu Ala Lys Leu Val Ile Phe
    290                 295                 300 act gga ctc atg gga ttt ata ata gag caa tat ata aat cct att gtt    960
Thr Gly Leu Met Gly Phe Ile Ile Glu Gln Tyr Ile Asn Pro Ile Val
305                 310                 315                 320 agg aac tca aag cat cct ctg aaa ggg gac ctt cta tat gct att gaa   1008
Arg Asn Ser Lys His Pro Leu Lys Gly Asp Leu Leu Tyr Ala Ile Glu
                325                 330                 335 aga gtg ttg aag ctt tca gtt cca aat cta tat gtg tgg ctc tgc atg   1056
Arg Val Leu Lys Leu Ser Val Pro Asn Leu Tyr Val Trp Leu Cys Met
            340                 345                 350 ttc tac tgc ttc ttc cac ctt tgg tta aac ata ttg gca gag ctc ctc   1104
Phe Tyr Cys Phe Phe His Leu Trp Leu Asn Ile Leu Ala Glu Leu Leu
```

-continued

```
                     355                      360                      365
tgc ttc ggg gac cgt gaa ttc tac aaa gat tgg tgg aat gca aaa agc      1152
Cys Phe Gly Asp Arg Glu Phe Tyr Lys Asp Trp Trp Asn Ala Lys Ser
370                     375                      380 gtt gga gat tat tgg aga atg tgg aat atg cct gtt cac aaa tgg atg      1200
Val Gly Asp Tyr Trp Arg Met Trp Asn Met Pro Val His Lys Trp Met
385                     390                      395                 400 gtt cga cat gta tac ttt ccg tgc ctg cgc atc aag ata cca aaa gta      1248
Val Arg His Val Tyr Phe Pro Cys Leu Arg Ile Lys Ile Pro Lys Val
                    405                      410                 415 ccc gcc att atc att gct tta gtc tct gca gtc ttt cat gag tta          1296
Pro Ala Ile Ile Ile Ala Phe Leu Val Ser Ala Val Phe His Glu Leu
                420                      425                      430 tgc atc gca gtt cct tgc cgt ctc ttc aat cta tgg gct ttc atg gga      1344
Cys Ile Ala Val Pro Cys Arg Leu Phe Asn Leu Trp Ala Phe Met Gly
            435                      440                      445 att atg ttt cag gtc cct ttg gtc ttt atc aca aac ttt tta caa gaa      1392
Ile Met Phe Gln Val Pro Leu Val Phe Ile Thr Asn Phe Leu Gln Glu
        450                      455                      460 agg ttt ggc tcc atg gtg gga aac atg atc ttt ggt tca gct tct tgc      1440
Arg Phe Gly Ser Met Val Gly Asn Met Ile Phe Gly Ser Ala Ser Cys
465                     470                      475                 480 att ttc gga caa ccg atg tgt ggg ctt ctt tat tac cat gac ctg atg      1488
Ile Phe Gly Gln Pro Met Cys Gly Leu Leu Tyr Tyr His Asp Leu Met
                    485                      490                 495 aac cgc aaa gga tcc atg tcc tga                                      1512
Asn Arg Lys Gly Ser Met Ser
                500

<210> SEQ ID NO 4
<211> LENGTH: 503
<212> TYPE: PRT
<213> ORGANISM: Brassica napus
<223> OTHER INFORMATION: DGAT1

<400> SEQUENCE: 4

Met Ala Ile Leu Asp Ser Gly Gly Val Ala Val Pro Pro Thr Glu Asn
1               5                   10                  15

Gly Val Ala Asp Leu Asp Arg Leu His Arg Arg Lys Ser Ser Ser Asp
            20                  25                  30

Ser Ser Asn Gly Leu Leu Ser Asp Thr Ser Pro Ser Asp Asp Val Gly
        35                  40                  45

Ala Ala Ala Ala Glu Arg Asp Arg Val Asp Ser Ala Ala Glu Glu Glu
    50                  55                  60

Ala Gln Gly Thr Ala Asn Leu Ala Gly Gly Asp Ala Glu Thr Arg Glu
65                  70                  75                  80

Ser Ala Gly Gly Asp Val Arg Phe Thr Tyr Arg Pro Ser Val Pro Ala
                85                  90                  95

His Arg Arg Thr Arg Glu Ser Pro Leu Ser Ser Asp Ala Ile Phe Lys
            100                 105                 110

Gln Ser His Ala Gly Leu Phe Asn Leu Cys Val Val Val Leu Val Ala
        115                 120                 125

Val Asn Ser Arg Leu Ile Ile Glu Asn Leu Met Lys Tyr Gly Trp Leu
    130                 135                 140

Ile Arg Thr Asp Phe Trp Phe Ser Ser Thr Ser Leu Arg Asp Trp Pro
145                 150                 155                 160

Leu Phe Met Cys Cys Leu Ser Leu Ser Val Phe Pro Leu Ala Ala Phe
                165                 170                 175
```

```
Thr Val Glu Lys Met Val Leu Gln Lys Phe Ile Ser Glu Pro Val Ala
            180                 185                 190

Ile Ile Leu His Val Ile Ile Thr Met Thr Glu Val Leu Tyr Pro Val
            195                 200                 205

Tyr Val Thr Leu Arg Cys Asp Ser Ala Phe Leu Ser Gly Val Thr Leu
            210                 215                 220

Met Leu Leu Thr Cys Ile Val Trp Leu Lys Leu Val Ser Tyr Ala His
225                 230                 235                 240

Thr Ser Tyr Asp Ile Arg Thr Leu Ala Asn Ser Ala Asp Lys Val Asp
                    245                 250                 255

Pro Glu Ile Ser Tyr Tyr Val Ser Leu Lys Ser Leu Ala Tyr Phe Met
            260                 265                 270

Val Ala Pro Thr Leu Cys Tyr Gln Pro Ser Tyr Pro Arg Ser Pro Cys
            275                 280                 285

Ile Arg Lys Gly Trp Val Ala Arg Gln Leu Ala Lys Leu Val Ile Phe
            290                 295                 300

Thr Gly Leu Met Gly Phe Ile Ile Glu Gln Tyr Ile Asn Pro Ile Val
305                 310                 315                 320

Arg Asn Ser Lys His Pro Leu Lys Gly Asp Leu Leu Tyr Ala Ile Glu
                    325                 330                 335

Arg Val Leu Lys Leu Ser Val Pro Asn Leu Tyr Val Trp Leu Cys Met
                340                 345                 350

Phe Tyr Cys Phe Phe His Leu Trp Leu Asn Ile Leu Ala Glu Leu Leu
            355                 360                 365

Cys Phe Gly Asp Arg Glu Phe Tyr Lys Asp Trp Trp Asn Ala Lys Ser
            370                 375                 380

Val Gly Asp Tyr Trp Arg Met Trp Asn Met Pro Val His Lys Trp Met
385                 390                 395                 400

Val Arg His Val Tyr Phe Pro Cys Leu Arg Ile Lys Ile Pro Lys Val
                    405                 410                 415

Pro Ala Ile Ile Ile Ala Phe Leu Val Ser Ala Val Phe His Glu Leu
                420                 425                 430

Cys Ile Ala Val Pro Cys Arg Leu Phe Asn Leu Trp Ala Phe Met Gly
            435                 440                 445

Ile Met Phe Gln Val Pro Leu Val Phe Ile Thr Asn Phe Leu Gln Glu
            450                 455                 460

Arg Phe Gly Ser Met Val Gly Asn Met Ile Phe Gly Ser Ala Ser Cys
465                 470                 475                 480

Ile Phe Gly Gln Pro Met Cys Gly Leu Leu Tyr Tyr His Asp Leu Met
                485                 490                 495

Asn Arg Lys Gly Ser Met Ser
            500

<210> SEQ ID NO 5
<211> LENGTH: 18
<212> TYPE: DNA
<213> ORGANISM: Arabidopsis thaliana

<400> SEQUENCE: 5
gctcccacat tgtgttat                                                     18

<210> SEQ ID NO 6
<211> LENGTH: 18
<212> TYPE: DNA
<213> ORGANISM: Arabidopsis thaliana
```

```
<400> SEQUENCE: 6
gaattcacga tccccgaa                                              18

<210> SEQ ID NO 7
<211> LENGTH: 6
<212> TYPE: PRT
<213> ORGANISM: Arabidopsis thaliana

<400> SEQUENCE: 7

Ala Pro Thr Leu Cys Tyr
  1               5

<210> SEQ ID NO 8
<211> LENGTH: 6
<212> TYPE: PRT
<213> ORGANISM: Arabidopsis thaliana

<400> SEQUENCE: 8

Phe Gly Asp Arg Glu Phe
  1               5

<210> SEQ ID NO 9
<211> LENGTH: 19
<212> TYPE: DNA
<213> ORGANISM: Brassica napus

<400> SEQUENCE: 9
agaacatgca gagccacac                                             19

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 10
gagaggtacc gaaatggcga ttttggattc                                 30

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 11
ctcgcggccg ctcatggatc ctttgcgg                                   28

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 12
gagaggtacc atgtgttgtc tctccctt                                   28

<210> SEQ ID NO 13
<211> LENGTH: 19
<212> TYPE: DNA
<213> ORGANISM: Brassica napus
```

```
<400> SEQUENCE: 13
tcatgtgttg tctctccct                                                      19

<210> SEQ ID NO 14
<211> LENGTH: 21
<212> TYPE: DNA
<213> ORGANISM: Brassica napus

<400> SEQUENCE: 14
ttttccaatt gaccaatttt t                                                   21

<210> SEQ ID NO 15
<211> LENGTH: 20
<212> TYPE: DNA
<213> ORGANISM: Brassica napus

<400> SEQUENCE: 15
gaaatggcga ttttggattc                                                     20

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: adapter

<400> SEQUENCE: 16
gagtcgactc tagaagcttt tttttttttt ttt                                      33

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: adapter

<400> SEQUENCE: 17
gagtcgactc tagaagct                                                       18
```

DIACYLGLYCEROL O-ACYLTRANSFERASE

FIELD OF THE INVENTION

The invention relates to the field of molecular biology. In particular, the invention relates to isolated polynucleotides encoding diacylglycerol O-acyltransferase.

BACKGROUND OF THE INVENTION

Oils obtained from plant seeds are important sources of fatty acids for human consumption and for use as chemical feedstocks. These fatty acids include essential fatty acids, saturated fatty acids, monounsaturated fatty acids, and polyunsaturated fatty acids. In plant seed oils, fatty acids are stored predominantly as triacylglycerols (TAGs). TAGs represent the most efficient form of stored energy in eukaryotic cells.

TAG biosynthesis occurs in the endoplasmic reticulum, in plastids, and in oil bodies, and uses sn-glycerol-3-phosphate and acyl-CoAs as its primary substrates (Stymne and Stobart, 1987; Oo and Chew, 1992; Frentzen, 1993). Biosynthesis of TAG is effected through a biochemical process generally known as the Kennedy pathway, and involves the stepwise esterification of three fatty acyl moieties to the glycerol backbone, the fatty acyl moieties being derived from acyl CoA. Each step is catalyzed by a different acyltransferase. Prior to the final acylation, the phosphate at the sn-3 position of sn-1,2-diacylglycerol phosphate (phosphatidate) is removed via the catalytic action of phosphatidate phosphatase. The final step is the acylation of sn-1,2-diacylglycerol (DAG) by diacylglycerol O-acyltransferase (DGAT; EC 2.3.1.20) to form TAG. The acylation of DAG to form TAG, catalyzed by DGAT, is the only committed step in the Kennedy pathway, and it has been suggested that DGAT may be rate limiting in plant storage lipid accumulation (Ichihara et al., 1988; Perry and Harwood, 1993; Settlage et al., 1998).

In view of its potential rate-limiting function, it has been suggested that DGAT is a potential target in the genetic modification of plant lipid biosynthesis. For instance, increased DGAT abundance in plant oilseeds could lead to increased seed oil content and improvements in the fatty acid composition of the oil. Further, because DAG is an important signaling molecule that activates protein kinase C, DGAT activity may potentially affect cellular signal transduction.

DGAT is also present in animal cells, and has been identified as perhaps being involved in: (a) intestinal fat absorption; (b) lipoprotein assembly and the regulation of plasma TAG concentrations; (c) fat storage in adipocytes; (d) energy metabolism in muscle; (e) milk production; and, (f) egg production, including the production of mammalian oocytes. Genetic manipulation of DGAT may be useful in affecting these traits. For instance, regulation of DGAT activity could have value in changing the marbling characteristics in beef, resulting in meat cuts of higher quality and commercial value.

Kamisaka et al. (1997) describe purification of DGAT from *Mortierella ramanniana* var. angulispora. Additionally, a few isolated DGAT coding sequences are known. Cases et al. (1998) disclose a predicted amino acid sequence of murine DGAT, and a corresponding coding sequence is disclosed in GenBank Accession No. AF078752. GenBank Accession Nos.AJ131831 (Hills et al., 1999) and AJ238008 (Zou et al., 1999) provide DGAT coding sequences of *Arabidopsis thaliana*. However, to the knowledge of the applicants, the prior art does not disclose *Brassica napus* (canola) DGAT coding sequences or polypeptides.

It appears that *B. napus* might contain as many as four or five different DGAT genes. Although DGAT catalyzes only a single reaction, i.e. the acylation of DAG to TAG, the chain-length of the acyl-CoA substrate may vary, as may the degree of saturation of the substrate. In *B. napus*, $C_{18}$ acyl-CoAs are predominant, and these may be saturated ($C_{18:0}$), monounsaturated ($C_{18:1}$), or polyunsaturated ($C_{18:2}$ or $C_{18:3}$). Isolated coding sequences for DGAT having specificity for unsaturated acyl-CoAs would be useful for producing more highly unsaturated TAGs, which have been shown to have human health benefits. Canola oil has the lowest saturation level (6–7%) of the common edible oils, even lower than soya or corn oil. Hence, canola oil is valued as a healthful oil for human consumption. However, the saturation level of canola oil has been slowly increasing over time, perhaps due to narrowing of the gene pool of *B. napus* strains currently cultivated. The result is that soya- or corn-based oil products have become more competitive with respect to saturation level. Transformation of *B. napus* with polynucleotides encoding DGAT having specificity for unsaturated acyl-CoAs may be a strategy for reducing the saturation level of canola oil.

Moreover, over-expression of DGAT in *B. napus* or other oilseed plants, irrespective of its acyl-CoA specificity, would have the benefit of increasing TAG production in the plant. Use of native *B. napus* DGAT coding sequences for over-expression of DGAT in *B. napus* would be particularly advantageous because some of the concerns surrounding genetically modified organisms (GMOs) might be avoided. It will therefore be to value to isolate various *B. napus* DGAT genes.

SUMMARY OF THE INVENTION

The invention provides isolated polynucleotides (hereinafter described as "DGAT polynucleotides") which encode polypeptides having DGAT activity and which comprise amino acid sequences having at least 95% sequence identity, and more preferably 98% sequence identity, to the amino acid sequence depicted in SEQ ID NO: 2, or having at least about 95% sequence identity, and more preferably at least about 98% sequence identity, to the amino acid sequence depicted in SEQ ID NO: 4, and which have a length of at least 300 amino acid residues, preferably at least 400 amino acid residues, and even more preferably at least 500 amino acid residues. Preferably, the isolated DGAT polynucleotide encodes a full-length naturally-occurring *Brassica napus* DGAT. In an exemplified case, the isolated DGAT polynucleotide encodes the amino acid sequence depicted in SEQ ID NO: 2. In another exemplified case, the isolated DGAT polynucleotide encodes the amino acid sequence depicted in SEQ ID NO: 4.

The invention further provides polynucleotide constructs, vectors, and cells comprising DGAT polynucleotides.

The invention also provides isolated polypeptides having DGAT activity (hereinafter described as "DGAT polypeptides"), and which are encoded by the isolated DGAT polynucleotides of the invention.

Also provided are transgenic plants, plant cells, callus, seeds, plant embryos, microspore-derived embryos, and microspores, comprising DGAT polynucleotides.

The invention also provides methods for making recombinant plants comprising DGAT polynucleotides, methods for producing DGAT, and methods for modulating DGAT activity in plants.

The invention further provides methods for producing oils, and methods for producing TAGs.

The compositions and methods of the invention are useful in a wide range of industrial, agricultural, and medical applications. In particular, the compositions and methods of the invention are useful for improving seed oil content and fatty acid composition in plants, particularly *Brassica napus*. Use of isolated *B. napus*-derived DGAT polynucleotides of the invention for the over-expression of DGAT in *B. napus* is particularly useful, as it may avoid at least some of the concerns over GMOs.

BRIEF DESCRIPTION OF THE DRAWINGS

The FIG. 1 depicts an amino acid sequence alignment between full length BnDGAT1 (SEQ ID NO: 4) and full length BnDGAT2 (SEQ ID NO: 2), which are both exemplified DGAT polypeptides of the invention. The BnDGAT1 amino acid sequence is in the upper row and the BnDGAT2 sequence is in the lower row. The sequence alignment was generated with the BESTFIT program (Henikoff et al., 1992). The percentage sequence similarity was 97.1 and the percentage sequence identity was 96.2. Details of the alignment are as follows: scoring matrix BLOSUM 62 was used; the gap weight was 8; and the length weight was 2. Match display thresholds for the alignment are: "|"=identity; ":"=2; and "."=1.

DETAILED DESCRIPTION OF THE INVENTION

Definitions

In order to provide a clear and consistent understanding of the specification and claims, including the scope to be given to such terms, the following definitions are provided.

Unless the context clearly dictates otherwise, the singular forms "a," "an," and "the," encompass the plural.

A "coding sequence" is the part of a gene which codes for the amino acid sequence of a protein, or for a functional RNA such as a tRNA or rRNA.

A "complement" or "complementary sequence" is a sequence of nucleotides which forms a hydrogen-bonded duplex with another sequence of nucleotides according to Watson-Crick base-pairing rules. For example, the complementary base sequence for 5'-AAGGCT-3' is 3'-TTCCGA-5'.

"DGAT" means an enzyme of the class EC 2.3.1.20. DGAT catalyzes the reaction: acyl-CoA+sn-1,2-diacylglycerol→CoA+triacylglycerol. The official name of DGAT is diacylglycerol O-acyltransferase. Alternative names that are also used in the art include: (a) diglyceride acyltransferase; (b) diacylglycerol acyltransferase; and, (c) acyl-CoA:diacylglycerol acyltransferase.

A polypeptide having "DGAT activity" or having the "biological activity of DGAT" is a polypeptide that has, to a greater or lesser degree, the enzymatic activity of DGAT.

"Downstream" means on the 3' side of any site in DNA or RNA.

"Expression" refers to the transcription of a gene into structural RNA (rRNA, tRNA) or messenger RNA (mRNA) with subsequent translation into a protein.

Two polynucleotides or polypeptides are "functionally equivalent" if they perform substantially the same biological function. For instance, two polynucleotides are functionally equivalent if both encode the same DGAT.

Two polynucleotides are "heterologous" to one another if they are present in an arrangement other than that in which they occur in nature. Heterologous polynucleotides may be derived from the same organism, from different individuals within a species, or from organisms of different species.

Two polynucleotides or polypeptides are "identical" if the sequence of nucleotides or amino acid residues, respectively, in the two sequences is the same when aligned for maximum correspondence as described herein. Sequence comparisons between two or more polynucleotides or polypeptides are generally performed by comparing portions of the two sequences over a comparison window to identify and compare local regions of sequence similarity. The comparison window is generally from about 20 to about 200 contiguous nucleotides or contiguous amino acid residues. The "percentage of sequence identity" for polynucleotides and polypeptides may be determined by comparing two optimally aligned sequences over a comparison window, wherein the portion of the polynucleotide or polypeptide sequence in the comparison window may include additions or deletions (i.e., gaps) as compared to the reference sequence (which does not comprise additions or deletions) for optimal alignment of the two sequences. The percentage is calculated by: (a) determining the number of positions at which the identical nucleic acid base or amino acid residue occurs in both sequences to yield the number of matched positions; (b) dividing the number of matched positions by the total number of positions in the window of comparison; and, (c) multiplying the result by 100 to yield the percentage of sequence identity.

Optimal alignment of sequences for comparison may be conducted by computerized implementations of known algorithms, or by inspection. A list providing sources of both commercially available and free software is found in Ausubel et al. (2000). Readily available sequence comparison and multiple sequence alignment algorithms are, respectively, the Basic Local Alignment Search Tool (BLAST) (Altschul et al., 1990; Altschul et al., 1997) and ClustalW programs. BLAST is available on the Internet at http://www.ncbi.nlm.nih.gov and a version of ClustalW is available at http://www2.ebi.ac.uk. Other suitable programs include GAP, BESTFIT, FASTA, and TFASTA in the Wisconsin Genetics Software Package (Genetics Computer Group (GCG), 575 Science Dr., Madison, Wis.), or LALIGN (Genestream, www2.igh.cnrs.fr). For greater certainty, as used herein and in the claims, "percentage of sequence identity" of amino acid or nucleotide sequences is determined based on optimal sequence alignments determined in accordance with the default values of the BLAST program, available as described above. Unless otherwise specified, sequence alignments are based on a comparison of the full length of each sequence.

Identity between nucleotide sequences can also be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology. All hybridization methods (discussed in detail in Sambrook et al., 1989; and in Ausubel et al., 2000) depend on the ability of denatured DNA to re-anneal when complementary strands are present in an environment near, but below, their melting temperature ($T_m$), the temperature at which fifty percent of existing DNA duplex molecules are dissociated into single strands. A number of annealing reactions occur during hybridization. These include: annealing of the probe to homologous DNA sequences; mis-matched annealing of the probe to partially homologous sequences; and nonsequence specific interactions, which result in background noise. Mis-matched sequences form less stable hybrids than do completely homologous sequences. As a general rule, the $T_m$ of a double-stranded DNA molecule decreases by 1–1.5° C. with every 1% decrease in homology. Increases in temperature, and decreases in salt concentration disfavour annealing, and increase the stringency of the assay. Therefore, hybridization and wash conditions can be adjusted to achieve desired levels of annealing.

Hybridization is typically carried out in solutions of high ionic strength (e.g. 6×SSC (20×SSC=3.0 M NaCl, 0.3 M trisodium citrate 2H$_2$O, pH 7.0) or 6×SSPE (20×SSPE=3.0 M NaCl, 0.2 M NaH$_2$PO$_4$.H$_2$O, 20 mM EDTA, pH 7.4) at a temperature 20–25° C. below $T_m$. For Na$^+$ concentrations in the range of 0.01 M to 0.4 M, and G+C content from about 30–70%, $T_m$ of hybrids of greater than 100 nucleotides in length can be estimated by the equation $T_m$=81.5° C.–16.6 (log$_{10}$[Na$^+$])+0.41(%G+C)–0.63(% formamide)–(600/l), where l=the length of the hybrid in base pairs (bp). This equation applies to the "reversible" $T_m$ defined by measurement of hyperchromicity at OD$_{257}$. The "irreversible" $T_m$, which is more important for autoradiographic detection of DNA hybrids is usually 7–10° C. higher. (Sambrook et al., 1989). A convenient formula for estimating hybridization temperature ($T_h$) provided in product literature for NYTRAN brand nylon membranes is $T_h$=$T_m$–5° C.=2° C. (A–T bp)+4° C. (G–C bp)–5° C. To avoid background problems, hybridization time and the amount of probe used should be minimized. The probe preferably has a high specific activity and a length of at least about 50 nucleotides.

Washing is performed to remove excess probe, as well as probes that are bound as mis-match hybrids having less than a desired homology level. Washing proceeds in the order from least stringent to most stringent conditions. The stringency of the wash conditions can be varied by adjusting the temperature and salt concentrations of the wash solution. These conditions can be determined empirically by preliminary experiments in which samples of the DNA to be probed are immobilized on filters, hybridized to the probe, and then washed under conditions of different stringencies. By way of illustration, a typical low stringency wash may be conducted at room temperature in a solution of 2×SSC and 0.1% SDS (sodium dodecyl sulfate). A typical high stringency wash may be conducted at 68° C. in a solution of 0.1×SSC and 0.1% SDS.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated", but the same polynucleotide or polypeptide separated from the coexisting materials of its natural state is "isolated", as the term is employed herein.

Two DNA sequences are "operably linked" if the nature of the linkage does not interfere with the ability of the sequences to effect their normal functions relative to each other. For instance, a promoter region would be operably linked to a coding sequence if the promoter were capable of effecting transcription of that coding sequence.

A "polynucleotide" is a linear sequence of deoxyribonucleotides (in DNA) or ribonucleotides (in RNA) in which the 3' carbon of the pentose sugar of one nucleotide is linked to the 5' carbon of the pentose sugar of the adjacent nucleotide via a phosphate group.

A "polynucleotide construct" is a nucleic acid molecule which is isolated from a naturally occurring gene or which has been modified to contain segments of nucleic acid which are combined and juxtaposed in a manner which would not otherwise exist in nature.

A "polypeptide" is a linear polymer of amino acids that are linked by peptide bonds.

A "promoter" is a cis-acting DNA sequence, generally 80–120 bp long and located upstream of the initiation site of a gene, to which RNA polymerase may bind and initiate correct transcription.

A "recombinant" polynucleotide, for instance a recombinant DNA molecule, is a novel nucleic acid sequence formed in vitro through the ligation of two or more nonhomologous DNA molecules (for example a recombinant plasmid containing one or more inserts of foreign DNA cloned into its cloning site or its polylinker).

"transformation" means the directed modification of the genome of a cell by the external application of purified recombinant DNA from another cell of different genotype, leading to its uptake and integration into the subject cell's genome. In bacteria, the recombinant DNA is not integrated into the bacterial chromosome, but instead replicates autonomously as a plasmid.

A "transgenic" organism, such as a transgenic plant, is an organism into which foreign DNA has been introduced, or in which native DNA has been introduced or manipulated "by the hand of man" such that it exists in an arrangement or juxtaposition other than it exists in nature. A "transgenic plant" encompasses all descendants, hybrids, and crosses thereof, whether reproduced sexually or asexually, and which continue to harbour the foreign DNA or non-naturally occurring arrangement of DNA.

"Upstream" means on the 5' side of any site in DNA or RNA.

A "vector" is a nucleic acid molecule that is able to replicate autonomously in a host cell and can accept foreign DNA. A vector carries its own origin of replication, one or more unique recognition sites for restriction endonucleases which can be used for the insertion of foreign DNA, and usually selectable markers such as genes coding for antibiotic resistance, and often recognition sequences (e.g. promoter) for the expression of the inserted DNA. Common vectors include plasmid vectors and phage vectors.

DGAT Polynucleotides and DGAT Polypeptides

The invention provides isolated DGAT polynucleotides and DGAT polypeptides. DGAT polynucleotides of the invention include, without limitation: (1) single- or double-stranded DNA, such as complementary DNA (cDNA) or genomic DNA, and include both or either of the sense and antisense strand; and (2), RNA, such as messenger RNA (mRNA). DGAT polynucleotides of the invention include at least a coding sequence which codes for the amino acid sequence of the specified DGAT polypeptide, but may also include untranslated 3' and 5' regions that are present in the mature mRNA, or also transcriptional or translational regulatory elements such as promoters, enhancers, etcetera, which are found upstream or downstream from the transcribed region.

In an exemplified case, the invention provides a DGAT polynucleotide which is a complementary DNA (cDNA) comprising the nucleotide sequence depicted in SEQ ID NO: 1, and which was isolated from *Brassica napus*. The cDNA is 1446 bp in length, and includes a complete open reading frame (ORF) of 1026 bp (SEQ ID NO: 1 from nucleotide 82 to nucleotide 1107), and untranslated 5' and 3' regions of 81 and 339 nucleotides, respectively. The DGAT encoded by the ORF (designated herein as BnDGAT2; SEQ ID NO: 2) is a 341 amino acid protein having a predicted molecular weight of 39,532 Daltons (Da) and a basic isoelectric point of 8.96.

In another exemplified case, the invention provides a DGAT polynucleotide which is a cDNA comprising the nucleotide sequence depicted in SEQ ID NO: 3, which was also isolated from B. napus. The cDNA is 1512 bp in length, and encodes a complete ORF. The DGAT encoded by the ORF (designated herein as BnDGAT1; SEQ ID NO: 4) is a 503 amino acid protein with a predicted molecular weight of 56,931 Da, and a basic isoelectric point of 8.41.

It will be appreciated by those of skill in the art that, due to the degeneracy of the genetic code, numerous functionally equivalent nucleotide sequences encode the same amino acid sequence. Therefore, all DGAT polynucleotides that encode the DGAT polypeptides depicted in SEQ ID NOs: 2 and 4 are included in the invention.

It is known that proteins may be modified by certain amino acid substitutions, additions, deletions, and post-translational modifications, without loss or reduction of biological activity. In particular, it is well-known that conservative amino acid substitutions, that is, substitution of one amino acid for another amino acid of similar size, charge, polarity and conformation, are unlikely to significantly alter protein function. The 20 standard amino acids that are the constituents of proteins can be broadly categorized into four groups of conservative amino acids on the basis of the polarity of their side chains R- groups) as follows: the nonpolar (hydrophobic) group includes alanine, isoleucine, leucine, methionine, phenylalanine, proline, tryptophan and valine; the polar (uncharged, neutral) group includes asparagine, cysteine, glutamine, glycine, serine, threonine and tyrosine; the positively charged (basic) group contains arginine, histidine and lysine; and the negatively charged (acidic) group contains aspartic acid and glutamic acid. Substitution in a protein of one amino acid for another within the same group is unlikely to have an adverse effect on the biological activity of the protein.

The FIGURE depicts a sequence alignment between the amino acid sequences of Brassica napus BnDGAT1 of the invention (SEQ ID NO: 4) and B. napus BnDGAT2 of the invention (SEQ ID NO: 2). The polypeptides have about 96% sequence identity. As demonstrated in Example 3 herein, despite the sequence differences in their amino acid sequences, expression of both BnDGAT1 and BnDGAT2 in Pichia pastoris resulted in increased DGAT activity. Without being bound by same, it is believed that BnDGAT1 and BnDGAT2 represent the products of two different, but highly related DGAT genes of B. napus.

It is well-known in the art that individual amino acids or sequences of amino acids that are essential to the biological activity of a protein are closely conserved amongst related proteins, in accordance with principles of natural selection. Thus, those of skill in the art will recognize that substitutions, additions, deletions, and modifications of amino acids within the BnDGAT1 and BnDGAT2 sequences at non-conserved positions or regions will be less likely to negatively affect the enzymatic function of the protein than would equivalent changes within highly conserved regions. As such, it is expected that substitutions, additions deletions, and modifications would be least likely to negatively affect the DGAT activity of the exemplified DGAT polypeptides if the changes were to occur in a subregion where there is little or no conservation of the amino acid sequence.

Further, it will be noted in the Figure that BnDGAT2 is substantially shorter than BnDGAT1 (341 amino acids versus 503 amino acids), and that the region of sequence homology is between amino acids 163 to 503 of BnDGAT1, and amino acids 1 to 341 of BnDGAT2. The exemplified cDNA encoding BnDGAT2 may be incomplete, and lack a portion encoding the N-terminal region of the encoded DGAT. Nevertheless, the encoded product exhibited DGAT activity. This suggests that a fragment of the BnDGAT1 amino acid sequence, truncated at the N-terminal end (i.e. missing at least the first 162 amino acids) would also retain activity.

Hence, in accordance with the invention, those of ordinary skill in the art may obtain variant DGAT polypeptides having at least about 95% sequence identity, and more preferably at least about 98% sequence identity, with the exemplified DGAT polypeptide depicted in SEQ ID NO: 2, or having at least about 95% sequence identity, and more preferably at least about 98% sequence identity, with the exemplified DGAT polypeptide depicted in SEQ ID NO: 4, using known techniques. For instance, variant DGAT polypeptides may be obtained by mutagenesis of the polynucleotides depicted in SEQ ID NOs: 1 and 3. Useful mutagenesis techniques known in the art include, without limitation, oligonucleotide-directed mutagenesis, region-specific mutagenesis, linker-scanning mutagenesis, and site-directed mutagenesis by PCR (see e.g. Sambrook et al., 1989 and Ausubel et al., 2000). In addition, oligo-chimeric DNA techniques as described by Zhu et al. (1999) and Beetham et al. (1999) may be used to modify plant genes. Methods for determining the percentage of sequence identity between or amongst polypeptides and polynucleotides are known in the art, and are reviewed in the above Definitions section. Altered DGAT polypeptides can be tested for DGAT activity by the assay described in Example 3 herein.

Further, strains or varieties of B. napus may contain naturally occurring alleic variants of the DGAT genes which encode naturally occurring variants of the exemplified DGAT polypeptides depicted in SEQ ID NO: 2 and 4. All such allelic variants of the exemplified DGAT polynucleotides and the encoded DGAT polypeptides, in isolated form, are included within the scope of the invention, provided that the encoded DGAT polypeptides having at least about 95% sequence identity with the amino acid sequence depicted in SEQ ID NO: 2 or at least about 95% sequence identity with the amino acid sequence depicted in SEQ ID NO: 4.

Isolated DGAT polypeptides of the invention include polypeptides that have not undergone post-translational modification, as well as those that have been altered after their synthesis, whether naturally or otherwise, by, for example, phosphorylation, acetylation, ADP-ribosylation, glycosylation, or oxidation. DGAT polypeptides of the invention also include fusion proteins, wherein the DGAT polypeptide can be fused to a peptide or protein of interest.

DGAT polypeptides of the invention can be readily produced and isolated. For instance, Pichia pastoris can be transformed with a DGAT polynucleotide of the invention and the encoded DGAT polypeptide expressed as in Example 3 herein. Transformed microbial cells may be grown by a variety of known techniques including batch and continuous fermentation on liquid or semi-solid media (Gerhardt et al., 1994). Transformed cells are propagated under conditions optimized for maximum product-to-cost ratios. Product yields may be dramatically increased by manipulation of cultivation parameters such as temperature, pH, aeration, and media composition. Low concentrations of a protease inhibitor (e.g., phenylmethylsulfonyl fluoride or pepstatin) may be employed to reduce proteolysis of the over-expressed peptide or protein. Alternatively, protease deficient host cells may be employed to reduce or eliminate degradation of the desired protein.

Following fermentation, the microbial cells may be removed from the medium through known down-stream processes such as centrifugation and filtration. If the desired product is secreted, it can be extracted from the nutrient medium. In the case of intracellular production, the cells are harvested and the product released by rupturing cells through the application of mechanical forces, ultrasound, enzymes, chemicals and/or high pressure. Production of an insoluble product, such as occurs in hyper-expressing E. coli systems, can be used to facilitate product purification. The product inclusions can be extracted from disrupted cells by centrifugation, and contaminating proteins may be removed by washing with a buffer containing various concentrations of a denaturant (e.g., 0.5 to 6 M urea, 0.1 to 1% sodium dodecyl sulfate or 0.5 to 4.0 M guanidine-HCl). The washed inclusions may be solubilized in solutions containing 6 to 8 M urea, 1 to 2% sodium dodecyl sulfate or 4 to 6 M guanidine-HCl. Solubilized product can be renatured by slowly removing denaturing agents during dialysis.

If necessary, various methods for purifying the product from microbial fermentation may be employed. These include precipitation (e.g., ammonium sulfate precipitation), chromatography (gel filtration, ion exchange, affinity liquid chromatography), ultrafiltration, electrophoresis, solvent-solvent extraction (e.g., acetone precipitation), combinations thereof, or the like. Protein purification techniques are known in the art, and appropriate protocols are described by Deutscher (1990), Harris and Angal (1989), Janson and Ryd én (1998), and Rosenberg (1996).

Expression of DGAT in Plants

The isolated DGAT polynucleotides of the invention are useful for effecting the recombinant expression of DGAT in plants. Plant species of interest include, without limitation, crops used for commercial oil production such as: canola, mustard, or rapeseed (Brassica spp.); safflower (Carthamus spp.); sunflower or sunola (sunwheat) (Helianthus spp.); flax (Linum spp.); corn (Zea mays); soybean (Glycine and Soja spp.); castor (Ricinus comminis); cocoa bean (Theobroma cacao); coconut (Cocos spp.); olive (Olea spp.); palm (Elaeis spp.); peanut (Arachis spp.); jojoba (Simmondsia spp.); and commercial nuts (eg. Macadamia, Brazil nut). Other plant species of interest include: cotton (Gossypium spp.); mouse ear crest (Arabidopsis thaliana); wheat (Triticum spp.); rye (Secale spp.); barley (Hordeum spp.); oats (Avena spp.); rice (Oryza spp.); potato (Solanum spp.); tomato (Lycopersicon spp.); tobacco (Nicotiana spp.); borage (Borago spp.) Crambe spp.; Cuphea spp.; Lesquerella and Limnanthes spp.; nasturtium (Tropaeolum spp.); Oenothera spp.; avocado (Persea spp.); coffee (Coffea spp.); Vernonia spp.; Cucurbita spp. (gourd, squash, pumpkin, watermelon, etc.). For instance, an increase in oil content of oats by as little as five or six percent by means of the invention would be of significant benefit in animal feed applications. Copy number dependent over-expression of DGAT by transformation of Brassica napus (canola) with an isolated B. napus DGAT polynucleotide of the invention is particularly advantageous, because such transgenic plants, which merely possess additional copies of coding sequences originally derived from B. napus, may more readily meet increasingly stringent controls on GMOs, and achieve public acceptance. The DGAT polynucleotides of the invention are also useful for effecting DGAT expression in other eukaryotic organisms, such as oleagineous fungal species (e.g. Mortierella spp.).

The first step in making transgenic plants is to prepare an appropriate vector. Suitable recombinant vectors include an expression cassette designed for initiating transcription of the DGAT polynucleotide in plants. Additional sequences can be included to allow the vector to be cloned in a bacterial or phage host. The vector will preferably contain a prokaryote origin of replication having a broad host range. A selectable marker may also be included to allow selection of bacterial cells bearing the desired construct. Suitable prokaryotic selectable markers include those that confer resistance to antibiotics such as ampicillin. Other DNA sequences encoding additional functions may also be present in the vector. For instance, in the case of Agrobacterium mediated transformation, T-DNA sequences will also be included for subsequent transfer to plant chromosomes.

For expression in plants, the recombinant expression cassette preferably contains, in addition to the desired sequence, a promoter region effective in plants, a transcription initiation site (if the sequence to be transcribed lacks one), and a transcription termination sequence. Unique restriction enzyme sites at the 5' and 3' ends of the cassette are typically included to allow for easy insertion into a pre-existing vector. Sequences controlling eukaryotic gene expression are well known in the art.

Transcription of DNA into mRNA is regulated by a region of DNA referred to as the promoter. The promoter region contains a sequence of bases that signals RNA polymerase to associate with the DNA, and to initiate the transcription of mRNA using one of the DNA strands as a template to make a corresponding complementary strand of RNA. Promoter sequence elements include the TATA box consensus sequence (TATAAT), which is usually 20 to 30 bp upstream of the transcription start site. In most instances the TATA box is required for accurate transcription initiation. The TATA box is the only upstream promoter element that has a relatively fixed location with respect to the start point.

Another consensus sequence, the CAAT box, is centered at −75, but can function at distances that vary considerably from the start point and in either orientation.

Another common promoter element is the GC box at −90 which contains the consensus sequence GGGCGG. It may occur in multiple copies and in either orientation.

Other sequences conferring tissue specificity, response to environmental signals, or maximum efficiency of transcription may also be found in the promoter region. Such sequences are often found within 400 bp of transcription initiation size, but may extend as far as 2000 bp or more. In heterologous promoter/structural gene combinations, the promoter is preferably positioned about the same distance from the heterologous transcription start site as it is from the transcription start site in its natural setting. However, some variation in this distance can be accommodated without loss of promoter function.

The particular promoter used in the expression cassette is not critical to the invention. Any of a number of promoters which direct transcription in plant cells is suitable. The promoter can be either constitutive, inducible, tissue specific, or temporal specific.

A number of promoters which are active in plant cells have been described in the literature. These include the nopaline synthase (NOS) and octopine synthase (OCS) promoters (which are carried on tumour-inducing plasmids of Agrobacterium tumefaciens), the caulimovirus promoters such as the cauliflower mosaic virus (CaMV) 19S and 35S and the figwort mosaic virus 35S-promoters, the light-inducible promoter from the small subunit of ribulose-1,5-bis-phosphate carboxylase (ssRUBISCO, a very abundant plant polypeptide), and the chlorophyll a/b binding protein gene promoter, a cryptic promoter (tCUP) from tobacco, etc. All of these promoters have been used to create various types of DNA constructs which have been expressed in plants.

The CaMV 35S promoter, which is used in one of the Examples herein, has been shown to be highly active and constitutively expressed in most tissues (Bevan et al., 1986). Other promoters which may be used include: (a) native *B. napus* DGAT gene promoters; (b) those that show enhanced or specific expression in immature seeds; (c) promoters normally associated with the expression of sequences expressed in maturating seeds such as those for seed storage proteins (Breen and Crouch, 1992; Scofield and Crouch, 1987); or (d) promoters encoding a polypeptide located in the single-layer membrane enclosing oil droplet organelles (van Rooijen and Moloney, 1994). Examples of these promoters include those for the genes napin and cruciferin (Breen and Crouch, 1992; Scofield and Crouch, 1987) and oleosin (van Rooijen and Moloney, 1994).

In addition to a promoter sequence, the expression cassette should also contain a transcription termination region downstream of the structural gene to provide for efficient termination. The termination region may be obtained from the same gene as the promoter sequence or may be obtained from different genes. In the exemplified cases, the nopaline synthase NOS 3' terminator sequence (Bevan et al. 1983) was used.

Polyadenylation is believed to have an effect on stabilizing mRNAs. Therefore, polyadenylation sequences are also commonly added to the vector construct if the mRNA encoded by the structural gene is to be efficiently translated (Alber and Kawasaki, 1982). Polyadenylation sequences include, but are not limited to the Agrobacterium octopine synthase signal (Gielen et al., 1984) or the nopaline synthase signal (Depicker et al., 1982).

The vector will also typically contain a selectable marker gene by which transformed plant cells can be identified in culture. Typically, the marker gene encodes antibiotic resistance or herbicide resistance. These markers include those that confer resistance to the antibiotics G418, hygromycin, bleomycin, kanamycin, gentamycin, and the bar gene which confers herbicide resistance. In exemplified cases, the marker genes confer resistance to kanamycin, and glufosinate ammonium herbicide (Wan and Lemaux, 1994). Those cells containing the vector will be identified by their ability to grow in a medium containing the particular selective agent.

The objective of plant transformation with one or more DGAT polynucleotides may be to enhance activity of DGAT in immature seeds or other tissues, and further to obtain enhanced accumulation of TAGs in mature seeds or other tissues. In this case, the DGAT polynucleotide is inserted in the sense orientation into the expression cassette. Alternatively, if the desired result is to decrease the activity of endogenous DGAT or other enzymes, and to decrease the accumulation of TAGs in mature seeds or other tissues, the DGAT polynucleotide, or a short fragment thereof (e.g. 12–25 nucleotides) can be inserted in the antisense orientation into expression cassette. For instance, it might be desirable to reduce DGAT activity and TAG accumulation in monocot species such as oat in order to reduce the lipid content in the seed used to manufacture breakfast cereals. The use of antisense oligonucleotides is well known in the art, and is described in such references as Stone-Sophia et al. (1999) and Henzi et al. (1999). DGAT activity can also be reduced through use of ribozymes specific to the DGAT polynucleotides of the invention. Ribozymes are RNA molecules having the enzymatic properties of a sequence-specific endoribonuclease and which catalyze the cleavage of single-stranded RNA substrates. They are useful for the sequence-specific cleavage of mRNAs and thus for the inhibition of gene expression. Techniques for making suitable ribozymes are described by Steinecke et al. (1992) and Wegener et al. (1 994).

Once an appropriate vector has been assembled, a variety of techniques are available for introducing foreign DNA into plant cells. In accordance with the invention, bombardment (Weeks et al., 1993; Wan and Lemaux, 1994; Cho et al., 1998) is a preferred methods for introducing DGAT polynucleotides into cell explants from monocotyledonous plants (e.g. barley, oat, wheat). For introduction of DGAT polynucleotides into cell explants from dicotyledonous plants (e.g. canola), Agrobacterium mediated transformation (Tingay et al., 1997; Trick and Finer, 1997) is a preferred technique. Preferred sources of tissue explants include scutella from immature embryos or other tissue undergoing rapid multiplication and differentiation (e.g. meristems, immature inflorescences, callus, microspores, microspore-derived embryos, cell suspensions, and protoplasts).

Other transformation techniques which are known in the art can also be used to transfer the recombinant DNA. For instance, the vector can be micro-injected directly into plant cells. Alternatively, nucleic acids may be introduced to the plant cell by high velocity ballistic penetration with small particles having the nucleic acid of interest embedded within the matrix of the particles. Fusion of protoplasts with lipid-surfaced bodies such as minicells, cells or lysosomes carrying the DNA of interest can be used. The DNA may also be introduced into plant cells by electroporation, wherein plant protoplasts are electroporated in the presence of plasmids carrying the expression cassette. A review of these techniques is found in Gelvin et al. (1994).

The above-mentioned Agrobacterium mediated transformation technique, which is particularly useful for transformation of dicots such as canola, is a form of vectored transformation that uses *Agrobacterium tumefaciens*. *A. tumefaciens* is a Gram-negative soil bacteria which causes a neoplastic disease known as crown gall in dicotyledonous plants. Induction of tumours is caused by tumour-inducing plasmids known as Ti plasmids. Ti plasmids direct the synthesis of opines or octopines in the infected plant. The opines or octopines are used as a source of carbon and/or nitrogen by the Agrobacteria.

The bacterium does not enter the plant cell, but transfers only part of the Ti plasmid, a portion called T-DNA. The T-DNA becomes stably integrated into the plant genome, where it expresses the functions needed to synthesize opines and to transform the plant cell. Virulence (Vir) genes on the Ti plasmid, outside of the T-DNA region, are necessary for the transfer of the T-DNA. The vir region, however, is not transferred. In fact, the vir region, although required for T-DNA transfer, need not be physically linked to the T-DNA and may be provided on a separate plasmid.

The tumour-inducing portions of the T-DNA can be interrupted or deleted without loss of the transfer and integration functions, such that normal and healthy transformed plant cells may be produced which have lost all properties of tumour cells, but still harbour and express certain parts of T-DNA, particularly the T-DNA border regions. Therefore, modified Ti plasmids, in which the disease causing genes have been deleted, may be used as vectors for the transfer of gene constructs of the present invention.

Transformation of plants cells with Agrobacterium and regeneration of whole plants typically involves either co-cultivation of Agrobacterium with cultured isolated protoplasts or transformation of intact cells or tissues with Agrobacterium. In an exemplified case, petiole explants from *Brassica napus* plantlets are transformed with Agrobacterium.

When it is desired to transform monocots such as wheat or barley with DGAT polynucleotides, biolistic transformation techniques are preferred. In such techniques, cauliflower mosaic virus (CaMV) may be used as a vector. For instance, U.S. Pat. No. 4,407,956 to Howell describes the use of CaMV as a plant vehicle. The CaMV transformation vector preferably includes a rice actin promoter and the first intron of the actin gene (which controls the expression of the bar gene), followed by the bar gene (which confers resistance to glufosinate ammonium herbicide) and the NOS terminator. A second similar vector is also prepared, in which the DGAT polynucleotide of interest is substituted for the bar gene. Plant tissues are co-transformed by bombardment with gold particles coated with both vectors. Co-transformation enables integration of vectors in different location of the genome which will lead to segregation of the marker gene from the gene of interest in subsequent generations when plants are regenerated.

Embryogenic tissue, such as immature scutella dissected from embryos, is preferred for bombardment (Cho et al., 1998; Wan and Lemaux, 1994). The embryonic tissue preferably is obtained from an easily regenerated plant line or cultivar (e.g. var. Golden Promise in barley). Using a micro-projectile bombardment device, embryogenic tissues are bombarded gold particles that are coated with the DNA constructs of interest, and plants are then regenerated (Wan and Lemaux, 1994).

After transformation, transformed plant cells or plants carrying the introduced DNA are identified, typically by selection for the marker gene. In exemplified cases, transformed plant cells are selected by growing the cells on growth medium containing kanamycin and glufosinate ammonium. Other selectable markers will be apparent to those of skill in the art. For instance, the presence of opines can be used to identify transformants if the plants are transformed with Agrobacterium.

Expression of the foreign DNA can be confirmed by detection of RNA encoded by the inserted DNA using well known methods such as Northern blot hybridization. The inserted DNA sequence can itself be identified by Southern blot hybridization or the polymerase chain reaction (PCR), as well, as described by Sambrook et al. (1989) and Ausubel et al. (2000).

Generally, after it is determined that the transformed plant cells carry the recombinant DNA, whole plants are regenerated. Suitable techniques for plant regeneration using different explanted tissues are described in the art (Lörz et al., 1998; Bommineni et al., 1997; Takumi and Shirnada, 1997; Yao et al., 1998; Kemper et al., 1996; Ritala et al., 1995; Nehra et al., 1994; Parrot et al., 1991; Moloney et al., 1989; De Block, 1988; Fraley et al., 1985, 1983; and U.S. Pat. Nos. 4,407,956, 4,666844, 5,589,617, 5,631,152, and 5,874,265).

In an exemplified case, cotyledon explants of *Brassica napus* cultures are inoculated via the petiole with a culture of *Agrobacterium tumefaciens* carrying the desired DNA and a kanamycin marker gene. Transformants are selected on a kanamycin-containing growth medium. After transfer to a suitable medium for shoot induction, shoots are transferred to a medium suitable for rooting. Plants are then transferred to soil and hardened off. The plants regenerated in culture are transplanted and grown to maturity under greenhouse conditions.

Regeneration of barley and other monocots typically involves two tissue culture steps, induction and regeneration, which are accomplished by culturing tissues on two successive media for predetermined time periods. The induction stage involves dedifferentiation of cells and induction of fast-growing embryogenic callus. At the callus stage, cells divide very rapidly, in an anarchic manner. The rapid cell division is controlled by high auxin concentration in the medium (2,4-D; 2,4,5-T; or dicamba alone), or alternatively by cytokinin (Cho et al., 1998). Masses of cells are allowed to grow on the same medium for a period of 20 to 30 days to favour constant growth of calli and to inhibit possible organogenesis. The cells are then transferred to fresh media, initially without light, but with light thereafter. Plant regeneration occurs when callus tissues are placed on a second medium that does not contain auxin (or contains much less auxin than the induction medium) and which contains cytokinin. The release of the auxin-mediated hormonal control allows the embryogenesis program to commence.

The screening of transformed tissues and regenerated plants can be accomplished by including in the media an appropriate chemical for selecting transformants carrying a marker gene introduced together with the DNA of interest. For example, glufosinate ammonium can be used to select tissues carrying the bar gene (Wan and Lemaux, 1994).

As they mature, developing embryos produce shoots and regenerated plantlets. Then masses of cells with green shoots are excised and placed on a rooting medium. Plantlets are then transferred to soil and are tested for the presence of the DGAT polynucleotide using either Southern blot analysis or PCR.

Recombinant DNA procedures used for practicing the invention and which are not described in detail herein involve standard laboratory techniques that are well known in the art and are described in standard references such as Sambrook et al. (1989) or Ausubel et al. (2000). Generally, enzymatic reactions involving DNA ligase, DNA polymerase, restriction endonucleases and the like are performed according to the manufacturer's specifications. Abbreviations and nomenclature employed herein are standard in the art and are commonly used in scientific publications such as those cited herein.

The invention is further illustrated by the following non-limiting Examples.

EXAMPLE 1

Isolation of a First DGAT Polynucleotide

A cDNA encoding a *Brassica napus* L. cv Jet Neuf DGAT (BnDGAT2) was isolated, and the predicted amino acid sequence determined.

A microspore-derived cell suspension culture from *Brassica napus* L. cv Jet Neuf was prepared (Orr et al., 1986; Weselake et al., 1998).

A 300 base pair (bp) internal cDNA fragment was amplified by RT-PCR (reverse transcription polymerase chain reaction) using the oligonucleotide primers 5'-GCTCCCACATTGTGTTAT-3' (DGATF1; SEQ ID NO: 5) and 5'-GAATTCACGATCCCCGAA-3' (DGATR1; SEQ ID NO: 6) from total RNA obtained from cells cultured in a 6% (w/v) sucrose containing media as described by Weselake et al. (1998). These primers correspond to the upstream conserved region APTLCY (SEQ ID NO: 7) and the downstream conserved region FGDREF (SEQ ID NO: 8) existing between mouse DGAT (GenBank Accession No. AF078752) and two putative *Arabidopsis thaliana* ACATs (GenBank Accession Nos. AC003058 and AC005917) (Lin et al., 1999). Sequence analysis amongst Arabidopsis ACATs and the 300 bp fragment revealed homology at the amino acid level.

Thereafter, 3' RACE (rapid amplification of cDNA ends) (Frohman, 1995) was employed using the DGATF1 primer with the adapter 5'-GAGTCGACTCTAGAAGCT-3' (ADP; SEQ ID NO: 17), following reverse transcription with 5'-GAGTCGACTCTAGAAGCTTTTTTTTTTTTTTTT-3' (ADPdT16; SEQ ID NO: 16). This resulted in a 1030 bp fragment corresponding to the 3' end and poly-A tail. For 5' RACE, total RNA was reverse transcribed with the gene specific primer DGATR1, and tailed with dATP using terminal transferase (TdT). An internal primer to the original 300 bp fragment designated DGATR2 (5'-AGAACATGCAGAGCCACAC-3') (SEQ ID NO: 9) was used in a 5' RACE reaction (Frohman, 1995) in combination with ADPdT16.

This resulted in an 850 bp fragment. The cDNA was cloned and sequenced, and was found to include a 240 bp overlap with the original 300 bp fragment and 3' clone. The cDNA therefore corresponded to the 5' end. A full length cDNA was then generated using gene specific primers 5'-TCATGTGTTGTCTCTCCCT-3' (DGAT2FLF; SEQ ID NO: 13) and 5'-TTTTCCAATTGACCAATTTTT-3' (DGATFLR; SEQ ID NO: 14) in a PCR amplification, revealing a 1446 bp cDNA having an ORF of 1026 bp.

The DNA sequence was obtained for all clones for both strands from subclones derived by T/A cloning into pGEM-T vector systems (Promega, Madison, Wis.). Sequencing was carried out at the University of Calgary Core DNA Service (Calgary, Alberta, Canada) with ABI Prism BigDye Terminator Cycle Sequencing Ready Reaction Kit (PE Applied Biosystems, Foster City, Calif.) using M13 forward and reverse primers.

Nucleotide and predicted amino acid sequence comparisons indicate that BnDGAT2 is related to published *Arabidopsis thaliana* sequences (Lin et al., 1999—GenBank Accession Nos. AC003058 and AC005917) and a *Mus musculus* sequence (Cases et al., 1998—GenBank Accession No. AF078752). Sequence alignments and homologies between species were obtained using the LALIGN program provided by GENESTREAM (www2.igh.cnrs.1r/home.eng.html).

The BnDGAT2 clone is 1446 bp in length, and includes a complete ORF of 1026 bp. The clone also contains untranslated 5' and 3' regions of 81 and 339 nucleotides respectively.

The ORF encodes a 341 amino acid protein with a predicted molecular weight of 39,532 Daltons (Da), and a basic isoelectric point of 8.96. The predicted translation and isoelectric point were obtained using the PROTPARAM tool and the topology was predicted using TMPRED, both provided at the ExPASy Molecular Biology Server (www.expasy.ch).

EXAMPLE 2

Isolation of a Second DGAT Polynucleotide

A full-length cDNA encoding a *Brassica napus* L. cv Jet Neuf DGAT (BnDGAT1) was isolated, and the predicted amino acid sequence determined.

A microspore-derived cell suspension culture from *Brassica napus* L. cv Jet Neuf was prepared as in Example 1. RACE was conducted as described in Example 1, using the internal primers designed against BnDGAT2 and total RNA from cells cultured in a 6% (w/v) sucrose containing media (Weselake et al., 1998). For 5' RACE, total RNA was reverse transcribed with the gene specific primer DGATR1 and tailed with dATP using terminal transferase (TdT). An internal primer designated DGATR2 was used in a 5'-RACE reaction in combination with an adaptor containing a poly-T tail (ADPdT16). This resulted in an 1500 bp fragment. The cDNA was cloned and sequenced and was found to be highly homologous to BnDGAT2 cDNA described in Example 1.

A full length cDNA was then generated using primers against the translation start site (5'-GAAATGGCGATTTTGGATTC-3'—DGATFLF; SEQ ID NO: 15) and a site near the translation stop site (DGATFLR), cloned and sequenced. The full length cDNA revealed a 1512 bp ORF.

The DNA sequence was obtained for both strands from a full length cDNA cloned into a pGEM-T vector (Promega, Madison, Wis.). Sequencing was carried out at the University of Calgary Core DNA Services (Calgary, Alberta, Canada) with ABI Prism BigDye Terminator Cycle Sequencing Ready Reaction Kit (PE Applied Biosystems, Foster City, Calif.) using M13 forward and reverse primers.

Nucleotide and predicted amino acid sequence comparisons indicate that BnDGAT1 is related to published *Arabidopsis thaliana* and *Mus musculus* sequences in GenBank, as described in the preceding Example. Related sequences were identified using Basic BLAST in the non-redundant sequence database (www.ncbi.nlm.nih.gov). Sequence alignments and homologies between species were obtained as in Example 1.

The BnDGAT1 clone is 1512 bp in length, and encodes a complete ORF. The ORF encodes a 503 amino acid protein with a predicted molecular weight of 56,931 Da, and a basic isoelectric point of 8.41. Predicted translation and isoelectric point were obtained as described in Example 1.

EXAMPLE 3

Expression of DGAT in *Pichia pastoris*

To demonstrate the biological activity of BnDGAT1 and BnDGAT2, the methylotrophic (capable of metabolizing methanol as its sole carbon source) *Pichia pastoris* strain GS115 (his4, Mut+; Invitrogen, San Diego, Calif.) was transformed with the pPICZ-A plasmid (Invitrogen, San Diego, Calif.) containing full length cDNAs corresponding to BnDGAT1 and BnDGAT2. The full length cDNA clones were used as the template to engineer Kpn1 and Not1 restriction sites by PCR for insertion into the multiple cloning site of pPICZ A (Invitrogen, San Diego, Calif.). For BnDGAT1, the primers used were DGAT1PIC for (5'-GAGA GGTACCGAAATGGCGATTTTGGATTC-3'; SEQ ID NO: 10), wherein the KpnI site, which is found just upstream of the translation start site, is underlined, and DGATPICrev (5'-CTCGCGGCCGCTCATGGATCCTTTGCGG-3'; SEQ ID NO: 11), wherein the NotI site is underlined. BnDGAT2 was amplitied in the same manner with the exception that DGAT2PIC for (5'-GAGA GGTACCATGTGTTGTCTCTCCCTT-3'; SEQ ID NO: 12) was used in combination with DGATPICrev. In order to ensure the insertion into pPICZ A was in frame at the 3' end with the myc epitope and polyhistidine tag, the translation stop site (5'-tga-3') was replaced with 5'-gcg-3' to encode asparagine. After double digests with the appropriate restriction enzymes, the fragments were separated on 1.5% agarose gels and sized. Fragments of the correct size were gel extracted with a gel extraction kit (Qiagen, Mississauga, Ontario, Canada). The restricted PCR products were then ligated into the *Pichia pastoris* expression vector pPICZ A (Invitrogen, San Diego, Calif.) precut with Kpn I/NotI. After transformation into Max Efficiency DH5α cells (Canadian Life Technologies, Burlington, Ontario) in accordance with the instructions of the manufacturer, cells were selected on zeocin plates. Colony PCR and size selection allowed the identification of positive clones which were subsequently sequenced using the 5'AOX1 and 3'AOX1 priming sites (Invitrogen, San Diego, Calif.) to ensure that the full length cDNAs were in frame and correct.

Recombinant plasmid vectors containing the full length cDNAs for BnDGAT1 and BnDGAT2 were isolated with Promega WIZARD PREPS (Promega, Madison, Wis.) and used to transform *P. pastoris* GS115 by electroporation. Prior to transformation, the isolated recombinant vectors were linearized with BstXI. Freshly prepared competent GS115 cells (80 μl) and linearized vector (10 μl) were combined in 0.2 cm pre-chilled cuvette cells (Bio-Rad) and incubated for 5 minutes on ice. Cells were pulsed using a charging voltage of 1.5 kV, capacitance of 25 (μF) and a resistance of 200 ohms. Thereafter, 1 ml of ice cold sorbitol (1 M) was added, and cells were incubated at 30° C. for 1 hour. Cells were plated to yeast/peptone/dextrose/sorbitol (YPDS) plus zeocin (100 μg/ml) and incubated for 2–4 days at 10° C. Recombinants were patched to fresh YPD plus zeocin plates and Mut+ recombinant yeast were identified by comparing growth rates on minimal dextrose medium+histidine (MDH; rapid growth) versus minimal methanol+histidine (MMH; slow growth) plates. The difference in growth rate is the result of the insertion of DGAT at the AOX1 gene locus. Expression of the recombinant gene is driven by the upstream alcohol oxidase (AOX1) promoter. Positive yeast clones were then grown in minimal glycerol medium+histidine (MGYH) overnight followed by the addition of 0.5% methanol and growth for an additional 24 hours, to induce expression. Recombinant yeast were then collected and assayed for DGAT activity as described below.

Harvested cells (250 mg) were ground with a glass homogenizer with four vols/gram tissue of grinding buffer consisting of 0.2 M HEPES-NaOH buffer, pH 7.4, containing 0.5 M sucrose. The resulting homogenate was collected in sterile microfuge tubes, flash frozen in liquid $N_2$ and stored at −80° C. DGAT in the homogenate (10 μL) was assayed for 10 min at 30° C. as described by Little et al. (1994), except that ATP and CoA were not included in the reaction mixture (Weselake et al., 1998). The reaction mixture (60 μL) consisted of 200 mM Hepes-NaOH buffer (pH 7.4) containing 3 mM $MgCl_2$, 330 μM sn-1,2-diolein, 15 mM[1-$^{14}$C]oleoyl-CoA (50 Ci/mole), 0.02% (w/v) TWEEN-20 and 6 mg BSA/mL. The protein content to the homogenate was determined using the Bio-Rad protein microassay based on the Bradford (1976) procedure, using BSA as the standard.

Control yeast were also collected, and were found to include non-transformed GS115 cells, and negative recombinant GS115 cells (GS115-a) that were transformed the vector with no insert (non-recombinant pPICZ-A). The results of the DGAT activity assay of transformed Pichia are set forth in the following table.

| DGAT Activity in homogenates of transformed *Pichia pastoris* | | | | |
|---|---|---|---|---|
| Time | GS 115[b] | GS 115-a[c] | BnDGAT1[d] | BnDGAT2[e] |
| 0 hours | 1[a] | 1 | 3 | 4 |
| 24 hours | 6 | 7 | 19 | 11 |

[a]pmol TAG/min/mg protein
[b]wild type *P. pastoris* (control)
[c]*P. pastoris* transformed with vector DNA only (control)
[d]*P. pastoris* transformed with BnDGAT1 cDNA
[e]*P. pastoris* transformed with BnDGAT2 cDNA It is apparent from the above table that the *P. pastoris* strain transformed with BNDGAT1 cDNA exhibited approximately 2.9 times the DGAT activity (in pmol TAG/min/mg protein) of the control *P. pastoris* strains, and that the *P. pastoris* strain transformed with BnDGAT2 cDNA exhibited approximately 1.7 times the DGAT activity of the control strains.

EXAMPLE 4

Expression of DGAT Polynucleotides in Dicots

A construct containing an isolated DGAT polynucleotide of the invention is engineered into the pBI121 vector that contains the CaMV 35S promoter (Kay et al., 1987) and the NOS 3' terminator sequence (Bevan et al., 1983). The pBI121 plasmid is composed of the following well-characterized segments of DNA. A 0.93 kb fragment isolated from transposon Tn7 which encodes bacterial spectinomycin/streptomycin (Spc/Str) resistance and is a determinant for selection in *E. coli* and *Agrobacterium tumefaciens* (Fling et al., 1985). This is joined to a chimeric kanamycin resistance gene engineered for plant expression to allow selection of the transformed tissue. The chimeric gene consists of the 0.35 kb cauliflower mosaic virus 35S promoter (P-35S) (Odell et al., 1985), the 0.83 kb neomycin phosphotransferase type II gene (NPTII), and the 0.26 kb 3' non-translated region of the nopaline synthase gene (NOS 3') (Fraley et al., 1983). The next segment is a 0.75 kb origin of replication from the RK2 plasmid (ori-V) (Stalker et al., 1981). It is joined to a 3.1 kb SalI to PvuI segment of pBR322 which provides the origin of replication for maintenance in *E. coli* (ori-322) and the bom site for the conjugational transfer in the *Agrobacterium tumefaciens* cells. Next is a 0.36 kb PvuI fragment from the pTiT37 plasmid which contains the nopaline-type T-DNA right border region (Fraley et al., 1985).

The vector containing the DGAT polynucleotide is transformed into the *B. napus* cultivar Westar according to the method of Moloney et al. (1989).

To prepare cotyledons for transformation, seeds are sterilized in 20% commercial bleach for 30 minutes while shaking. The seeds are then washed five times in a sterile funnel and filter paper using $ddH_2O$. The washed seeds are placed on *Brassica napus* I (BNI) seed germination medium (~20 per plate) (Moloney et al., 1989), wrapped in PARAFILM, and incubated at 25° C. for five days.

Agrobacterium harboring the plasmid of interest (e.g. pPZP (Hajdukiewicz et al., 1994) or another appropriate binary vector) is inoculated with 5 mL of Agrobacterium medium (AB) with a selection antibiotic and incubated at 28° C. for two days. Immediately prior to the transformation step, 1 mL of the Agrobacterium culture is spun down in a microfuge (13,000×g) for 1–2 minutes. The culture is resuspended in 1 mL of AB broth (no antibiotics) and diluted until $OD_{600}$=0.05.

Four to five day old cotyledons are used for transformation. The cotyledon is held with sterile forceps and cut with a sterile scalpel, without removing the apical meristem. Only a few cotyledons are cut at a time, and they are left on the germination plate to reduce dessication. The petiole of the cotyledon is dipped in the Agrobacterium suspension for 1 second and placed on BNII (co-cultivation) medium (Moloney et al., 1989). The petiole is pushed into the soft agar. To avoid growback, the cotyledon is not dipped a second time into the Agrobacterium suspension. Ten cotyledons are placed on each plate, and the plates are wrapped in PARAFILM and incubated in a growth room (25° C. with light) for two days.

The cotyledons are then transferred to BNIV (selection/regeneration) medium (Moloney et al., 1989), wrapped in PARAFILM, and incubated in a growth room. Agrobacterium growth is monitored during the first few weeks, and the tissue is transferred to new BNIV at the first sign of grow back of bacteria (approximately every second week). As soon as shoots arise from callus tissue, they are cut and placed on BNV (shoot elongation) medium (Moloney et al., 1989) in Magenta jars. Every second week, the shoots are transferred to fresh BNV medium. After the shoots have elongated, they are transferred to BNVI (rooting) medium (Moloney et al., 1989). Once the roots have formed, the plantlets are transferred to soil and placed in a misting chamber until NPTII enzymatic assays are done. NPTII positive plants are then and grown to maturity in a greenhouse growth chamber.

After enough leaf tissue has formed, Southern Blot analysis can be performed to verify presence of the DGAT polynucleotide gene. When seeds have formed, or at other stages of development, Northern and Western Blots can be performed, and enzymatic activity measured.

EXAMPLE 5

Expression of DGAT Polynucleotides in Monocots

The constructs used for transformation of monocots using the bombardment technique are similar to the constructs used for the transformation of dicots, and include a promoter, the DGAT polynucleotide, and a terminator gene segment.

The promoter is preferably a rice actin promoter and includes the 5' terminal end of the same actin gene including the first intron (McElroy et al., 1991). A DGAT polynucleotide is inserted in frame and followed by a 3' non-translated fragment of the NOS gene as terminator. This construct is identified as the pCORdgat construct. The bar gene conferring resistance to glufosinate ammonium (White et al., 1990) is used for selection. A pMB vector, such as pMB2 (Erickson et al., 1999), may be used. In this vector the bar gene is inserted in frame between the 35S promoter and the NOS terminator. Equal amount of the two constructs are used to coat gold particles before their acceleration into plant tissues.

Immature scutella are dissected from embryos of the barley cultivar Golden Promise and placed on the callus induction medium. Tissues are co-transformed with the pMB4 plasmid carrying the bar marker gene and the second pMB4 vector carrying the DGAT polynucleotide. DNA delivery to the tissues is carried out with the HELIOS Gene Gun System, a microprojectile bombardment device from Bio-Rad (#165-2431, 2000 Alfred Nobel Drive Hercules, Calif. USA 94547). An equal mass of these two plasmids (25 $\mu$g each) is mixed and coated on 25 mg of 1 $\mu$m gold particles and distributed on the inside wall of a 60-cm GOLDCOAT tubing according to the manufacturer's instructions. Discharge pressure is set at 125 psi and a diffusion screen (#165-2475) is used to ensure an even distribution of the gold particles carrying the plasmids. A similar particle delivery device, such as the Biolistic PDS-1000 He System (Bio-Rad #165-2257), or other functionally equivalent equipment can alternatively be used. The preparation of particles and pressure used are in accordance with the manufacturer's instructions for the instrument of choice.

The scutella are transferred to callus induction medium containing 5 mg/L of glufosinate ammonium salt (#C140300, Crescent Chemical, Hauppauge N.Y. USA), 16 h after bombardment. After 20–25 days, masses of cells are transferred to plant regeneration medium containing the same amount of selective agent as the previous medium. Embryos develop on the plant regeneration medium to produce shoots and regenerated plantlets. A mass of cells with green shoots are excised and placed on a rooting medium (without selective agent) to favour routing. Plantlets are then transferred to soil.

Herbicide-tolerant regenerated plants are tested with the leaf brush technique (LBT) using 500 mg/L of glufosinate ammonium salt, with an abundant brushing (Wan and Lamaux, 1994).

PCR product is probed to confirm presence of the bar gene or NPTII DNA in the plant cells, and PCR and Southern blot analyses are used to confirm the presence of the DGAT polynucleotide.

EXAMPLE 6

Lipid Analysis

Lipids are extracted from 500 mg samples of cells by the hexane/isopropanol procedure (Hara and Radin, 1978). After gravimetric determination, total extracted lipid is dissolved in 4 mL of hexane and stored at −20° C. in a Teflon-lined screw capped vial until subsequent methylation and further analysis via gas liquid chromatography (GLC). Extracted lipid is placed on ice and sonicated for 5 min. For each sample, two aliquots (0.25 mL) are transferred to separate screw-capped tubes. For one of the aliquots, the hexane is evaporated off under $N_2$ and set aside on ice. The remaining aliquot is used for the isolation of the TAG fraction. This aliquot (0.25 mL) is applied to Fertigplatten Kieselgel 60 plates and developed with one ascension of hexane/diethyl ether/acetic acid (80:20:1, v/v/v). A 50 mL aliquot of triolein (10 mg/mL) is used as a standard and visualized with iodine following thin-layer chromatography (TLC). The corresponding sections in lanes adjacent to the triolein standard are scraped into screw-capped tubes. To both the total extracted lipid and TAG fractions, 10 mL of pentadecanoic acid (C15:0; Sigma) (5 mg/2 mL hexane) are added as an internal standard. Methylation is carried out using 5 mL of methanolic HCl in sealed tubes at 50° C. for 24 h as described by Christie (1992). For TAG analysis, methylation is conducted in the presence of silica according to Browse et al. (1986), but with the use of methanolic-HCl as described above. After cooling, 0.25 mL water is added and the fatty acid methyl esters (FAMES) are extracted with two portions (5 mL each) of hexane. All samples are dried at 40° C. under a stream of $N_2$ and immediately suspended in 0.5 mL of hexane. Samples derived from total extracted lipid or TAG are transferred to GLC vials, capped tightly and analyzed for FAMES using a flame ionization gas chromatograph (Model 5890, Hewlett Packard, Mississauga, Ontario, Canada) equipped with a J and W Scientific 30-m DBR -23 Megabore column (Chromatographic Specialties, Brockville, Ontario, Canada) with helium as the carrier, at a low rate of 12 mL/min. Initial temperature is 180° C. for 5 min, increased to 230° C. by 2° C./min. Peaks are assigned by comparing retention times to those of FAME standards and relative proportions determined as percentages of summed peak areas. Values representing the proportion of TAG in total acyl lipid (TL) and the total extracted lipid (gravimetric determination) per g fresh weight are used to determine the TAG content of the cells on a FW basis.

REFERENCES

Alber, T. and Kawasaki, G. (1982) Nucleotide sequence of the triose phosphate isomerase gene of *Saccharomyces cerevisiae*. Journal of Molecular and Applied Genetics 1: 419–434.

Altschul, S. F., Gish, W., Miller, W., Myers, E. W. and Lipman, D. J. (1990) Basic local alignment search tool. Journal of Molecular Biology 215: 403–410.

Altschul, S. F., Madden, T. L., Schaffer, A. A., Zhang, J. H., Zhang, Z., Miller, W. and Lipman, D. J. (1997) GAPPED BLAST AND PSI-BLAST—A new generation of protein database search programs. Nucleic Acids Research 25: 3389–3402.

Ausubel, F. M., Bent, R., Kingston, R. E., Moore, D. J., Smith, J. A., Silverman, J. G. and Struhl K. (2000) Current Protocols in Molecular Biology. John Wiley & Sons, New York.

Beetham, P. R., Kipp, P. B., Sawycky, X. L., Arntzen, C. J. and May, G. D. (1999) A tool for functional plant genomics: Chimeric RNA/DNA oligonucleotides cause in vivo gene-specific mutations. Proceedings of the National Academy of Science U.S.A 96: 8774–8778.

Bevan, M. W., Flavell, R. B. and Chilton, M.-D. (1983) A chimaeric antibiotic resistance gene as a selectable marker for plant cell transformation. Nature (London) 304: 184–187.

Bevan M., Barker R., Goldsbrough, A., Jarvis, M., Kavanagh, T. and Iturriaga, G. (1986) The structure and transcription start site of a major potato tuber protein gene. Nucleic Acids Research 14: 4625–4638.

Bommineni, V. R., Jauhar, P. P. and Peterson, T. S. (1997) Transgenic durum wheat by microprojectile bombardment of isolated scutella. Journal of Heredity 88: 475–481.

Bradford, M. (1976) A rapid and sensitive method for the quantitation of microgram amounts of protein using the principle of protein-dye binding. Analytical Biochemistry 72: 248–254.

Breen, J. P. and Crouch, M. L. (1992) Molecular analysis of a Cruciferin storage protein gene family of *Brassica napus*. Plant Molecular Biology 19: 1049–1055.

Browse J., McCourt P. J. and Somerville, C. R. (1986) Fatty acid composition of leaf lipids determined after combined digestion and fatty acid methyl ester formation from fresh tissue. Analytical Biochemistry 152: 141–145.

Cases, S., Smith, S. J., Zheng, Y., Myers, H. M., Lear, S. R., Sande, E., Novak, S., Collins, C., Welch, C., Lusis, A. J. and Erickson, S. K. (1998) Identification of a gene encoding an acyl CoA:diacylglycerol acyltransferase, a key enzyme in triacylglycerol synthesis. Proceedings of the National Academy of Sciences USA 95:13018–13023.

Cho, M.-J., Jiang, W. and Lemaux, P. G. (1998) Transformation of recalcitrant barley cultivars through improvement of regenerability and decreased albinism. Plant Science 138: 229–244.

Christie, W. (1992) Preparation of fatty acid methyl esters. INFORM 3: 1031–1034.

De Block, M. (1988) Genotype-independent leaf disc transformation of potato (*Solanum tuberosum*) using *Agrobacterium tumefaciens*. Theoretical and Applied Genetics 76: 767–774.

Depicker, A., Stachel, S., Dhaese, P., Zambryski, P. and Goodman, H. M. (1982) Nopaline synthase: transcript mapping and DNA sequence *Agrobacterium tumefaciens*. Journal of Molecular and Applied Genetics 1: 561–573.

Deutscher, M. P. (1990) Guide to Protein Purification. Methods in Enzymology Volume 182. Academic Press, New York.

Erickson, F. L., Holzberg, S., Calderon-Urrea, A., Handley, V., Axtell, M., Corr, C. and Baker, B. 1999. The helicase domain of the TMV replicase proteins induces the N-mediated defence response in tobacco. The Plant Journal 18: 67–75.

Fling, M. E., Kopf, I. and Richards, C. (1985) Nucleotide sequence of the rtransposon Tn7 gene encoding an aminoglucoside-modifying enzyme 3" (9)-O-nucleotidyltransferase. Nucleic Acids Research 13: 7095–7106.

Fraley, R. T., Rogers, S. G., Horsch, R. B., Sanders, P. R., and Flick, J. S. (1983) Expression of bacterial genes in plant cells *Agrobacterium tumefaciens*. Proceedings of the National Academy of Sciences USA 80: 4803–4807.

Fraley, R. T., Rogers, S. G., Horsch, R. B., Eichholtz, D. A., Flick, J. S, Fink, C. L., Hoffmann, N. L., and Sanders, P. R. (1985) The SEV system: a new disarmed Ti plasmid vector system for plant transformation. Bio/Technology 3: 629–635.

Frentzen, M. (1993) Acyltransferases and triacylglycerols. In: Moore Jr., T. S. ed., Lipid metabolism in plants. Ann Arbor:CRC Press. pp. 195–230.

Frohman, M. A. (1995) Rapid amplification of cDNA ends. In PCR Primer A Laboratory Manual. Dieffenbach, C. W. and Dveksler G. S. eds., Cold Spring Harbor Laboratory Press, New York, pp. 381–409.

Gielen, J., De Beuckeleer, M., Seurinck, J., Deboeck, F., and De Greve, H. (1984) The complete nucleotide sequence of the TL-DNA of the *Agrobacterium tumefaciens* plasmid pTiAch5. EMBO Journal 3: 835–846.

Gelvin, S. B., Schilperoort, R. A. and Verma, D. P. S. (1994) Plant Molecular Biology Manual. Kluwer Academic Publishers. Belgium.

Gerhardt, P., Murray, R. G. E., Wood, W. A. and Krieg, N. R. (1994). Methods for General and Molecular Bacteriology. American Society for Microbiology. Washington, D.C., USA.

Hajdukiewicz, P., Svab, Z. and Maliga, P. (1994) The small, versatile pPZP family of Agrobacterium binary vectors for plant transformation. Plant Molecular Biology 25: 989–994.

Hara, A. and Radin, N. S. 1978. Lipid extraction of tissues with a low toxicity solvent. Analatycal Biochemistry 90: 420–426.

Harris, E. L. V. and Angal, S. (1989) Protein purification methods a practical approach. IRL Press, New York.

Henzi, M. X., Christey, M. C., McNeil, D. L. and Davies, K. M. (1999) Agrobacterium rhizogenes-mediated transformation of broccoli (*Brassica oleracea* L. var. italica) with an antisense 1-aminocyclopropane-1-carboxyicacid oxidase gene. Plant Science 143:55–62.

Henikoff, S. and Henikoff J. G. (1992) Amino acid substitution matrices from protein blocks. Proceedings of the National Academy of Sciences USA 89: 10915–10919.

Hills, M. J., Lu, C. and Hobbs, D. H. (Jun. 10, 1999) Arabidopsis thaliana mRNA for diacylglycerol O-transferase. GenBank Accession No. AF131831.

Ichihara, K., Takahashi, T. and Fujii, S. (1988) Diacylglycerol acyltransferase in maturing safflower seeds: its influence on the fatty acid composition of triacylglycerol and on the rate of triacylglycerol synthesis. Biochimica et Biophysica Acta 958:125–129.

Janson, J-C. and Ryden, L. (1998) Protein Purification. Prinicples, High-resolution Methods, and Applications. Wiley-Liss, New York.

Kamisaka, Y., Mishra, S. and Nakahara, T. (1997) Purification and characterization of diacylglycerol acyltransferase from the lipid body fraction of an oleaginous fungus. Journal Biochemistry 121:1107–1114.

Kay, R., Chan, A., Daly, M. and McPherson, J. (1987) Duplication of CaMV 35S orimoter sequences creates a strong enhancer for plant genes. Science 236: 1299–1302.

Kemper, E. L., da Silva, M. J. and Arruda, P. (1996) Effect of microprojectile bombardment parameters and osmotic treatment on particle penetration and tissue damage in transiently transformed cultured immature maize (*Zea mays* L.) embryos. Plant Science 121: 85–93.

Lin, X., Kaul, S., Rounsley, S. D., Shea, T. P., Benito, M.-I., Town, C. D., Fujii, C. Y., Mason, T. M., Bowman, C. L., Barnstead, M. E., Feldblyum, T. V., Buell, C. R., Ketchum, K. A., Lee, J. J., Ronning, C. M., Koo, H., Moffat, K. S., Cronin, L. A., Shen, M., VanAken, S. E., Umayam, L., Tallon, L. J., Gill, J. E., Adams, M. D., Carrera, A. J., Creasy, T. H., Goodman, H. M., Somerville, C. R., Copenhaver, G. P., Preuss, D., Nierman, W. C., White, O., Eisen, J. A., Salzberg, S. L., Fraser, C. M. and Venter, J. C. (1999) Sequence and analysis of chromosome 2 of the plant *Arabidopsis thaliana*. Nature 402:761–768.

Little, D., Weselake, R., Pomeroy, K., Furukawa-Stoffer T. and Bagu, J. (1994) Solubilization and characterization of diacylglycerol acyltransferase from microspore-derived cultures of oilseed rape. Biochemical Journal 303: 951–958.

Lörz, H., Becker, D. and Lütticke, S. (1998) Molecular wheat breeding by direct gene transfer. Euphytica 100: 219–223.

McElroy, D., Blowers, A. D., Jenes, B. and Wu, R. (1991) Construction of expression vectors based on the rice actin 1 (Act1) 5' region for use in monocot transformation. Molecular and General Genetics 231: 150–160.

Moloney, M. M., Walker, J. M. and Sharma, K. K. (1989) High efficiency transformation of *Brassica napus* using Agrobacterium vectors. Plant Cell Reports 8: 238–242.

Nehra, N. S., Chibbar, R. N., Leung, N., Caswell, K., Mallard, C., Steinhauer, L., Baga M. and Kartha, K. K. (1994) Self-fertile transgenic wheat plants regenerated from isolated scutellar tissues following microprojectile bombardment with two distinct gene constructs. The Plant Journal 5: 285–297.

Odell, J. T., Nagy, F. and Chua, N.-H. (1985) Identification of DNA sequences required for activity of the cauliflower mosaic virus 35S promoter. Nature 313: 810–812.

Oo, K-C. and Chew, Y-H. (1992) Diacylglycerol acyltransferase in microsomes and oil bodies of oil palm mesocarp. Plant Cell Physiology 33: 189–195.

Orr, W., Keller, W. A. and Singh, J. (1986) Induction of freezing tolerance in an embryogenic cell suspension culture of *Brassica napus* by abscisic acid at room temperature. Journal of Plant Physiology 126: 23–32.

Parrott, W. A., Merkle, S. A. and Williams, E. G. (1991) Somatic embryogenesis: Potential for use in propagation and gene transfer systems. In: Advanced Methods in Plant Breeding and Biotechnology, Murray D. R. (Ed.), CAB International, Wallingford, pp. 158–200.

Perry, H. J. and Harwood, J. L. (1993) Changes in the lipid content of developing seeds of *Brassica napus*. Phytochemistry 32:1411–1415.

Ritala, A., Aspegren, K., Kurtén, U., Salmenkallio-Marttila, M., Mannonen, L., Hannus, R., Kauppinen, V., Teeri, T. H. and Enari, T.-M. (1994) Fertile transgenic barley by particle bombardment of immature embryos. Plant Molecular Biology 24: 317–325.

Rosenberg, I. M. (1996) Protein Analysis and Purification. Benchtop Techniques. Birkhauser, Berlin.

Sambrook, J., Fritsch, E. F. and Maniatis, T. (1989) Molecular Cloning: A Laboratory Manual. Second ed. Cold Spring Harbor Press, New York.

Scofield, S. R. and Crouch, M. L. (1987) Nucleotide sequence of a member of the napin storage protein family from *Brassica napus*. The Journal of Biochemistry 262: 12202–12208.

Settlage, S. B., Kwanyuen, P. and Wilson, R. F. (1998) Relation between diacylglyceerol acyltransferase activity and oil concentration in soybean. Journal of American Oil Chemists Society 75: 775–781.

Stalker, D. M., Thomas, C. M. and Helinski, D. R. (1981) Nucleotide sequence of the region of the origin of replication of the broad host range plasmid RK2. Molecular and General Genetics 181: 8–12.

Steinecke, P., Herget, T. and Schreier, P. H. (1992) Expression of a chimeric ribozyme gene results in endonucleolytic cleavage of target mRNA and a concomitant reduction of gene expression in vivo. The EMBO Journal. 11: 1525–1530.

Stone-Sophia, L., Arnoldo, M. A. and Goring, D. R. (1999) A breakdown of Brassica self-incompatibibty in ARC1 antisense transgenic plants. Science 286:1729–1731.

Stymne, S. and Stobart, A. K. (1987) Triacylglycerol biosynthesis. In The Biochemistry of Plants, Vol. 9. Lipids: Structure and Function. Stumpf P. K. ed., Academic Press, New York, pp. 175–214.

Takumi, S. and Shimada, T. (1997) Variation in transformation frequencies among six common wheat cultivars through particle bombardment of scutellar tissues. Genes Genet. Syst. 72: 63–69.

Tingay, S., McElroy, D., Kalla, R., Fieg, S., Wang, M., Thornton, S., and Brettell, R. (1997) *Agrobacterium tumefaciens*-mediated barley transformation. The Plant Journal 11: 1369–1376.

Trick, H. N. and Finer, J. J. (1997) SAAT: sonication-assisted Agrobacterium-mediated transformation. Transgenic Research 6: 329–336.

van Rooijen, G. J. H. and Moloney, M. M. (1994) Plant seed oil-bodies as carriers for foreign proteins. Bio/Technology 13:72–77.

Wan, Y. and Lemaux, P. G. (1994) Generation of large numbers of independently transformed fertile barley plants. Plant Physiology 104: 37–48.

Weeks, J. T., Anderson, O. D. and Blechl, A. E. (1993) Rapid production of multiple independent lines of fertile transgenic wheat (*Triticum aestivum*). Plant Physiol. 102: 1077–1084.

Wegener, D., Steinecke, P., Herget, T., Petereit, I., Philipp, C. and Schreier, P. H. (1994) Expression of a reporter gene is reduced by a ribozyme in transgenic plants. Molecular and General Genetics 245: 465–470.

Weselake, R. J., Byers, S. D., Davoren, J. M., Laroche, A., Hodges, D. M., Pomeroy, M. K. and Furukawa-Stoffer, T.

L. (1998) Triacylglycerol biosynthesis and gene expression in microspore-derived cell suspension cultures of oilseed rape. Journal of Experimental Botany 49: 33–39.

White, J., Chang, S. Y., Bibb, M. J. and Bibb, M. J. (1990) A casssette containing the bar gene of *Streptomyces hygroscopious*: a selectable marker for plant transformation. Nucleic Acids Research 18:1062.

Yao, Q. A., Simion, E., William, M., Krochko, J. and Kasha, K. J. (1997) Biolistic transformation of haploid isolated microspores of barley (*Hordeum vulgare* L.). Genome 40: 570–581.

Zhu, T., Peterson, D. J., Tagliani, L., St. Clair, G., Baszczynski, C. L. and Bowen, B. (1999) Targeted manipulation of maize genes in vivo using chimeric RNA/DNA oligonucleotides. Proceedings of the National Academy of Science U.S.A 96: 8768–8773.

Zou, J., Wei, Y., Jako, C., Selvaraj, G. and Taylor, D. C. (Jun. 18, 1999). *Arabidopsis thaliana* mRNA for diacylglycerol 0-transferase. GenBank Accession No. AJ238008.

All publications mentioned in this specification are indicative of the level of skill in the art to which this invention pertains. To the extent they are consistent herewith, all publications mentioned in this specification are herein incorporated by reference to the same extent as if each individual publication was specifically and individually indicated to be incorporated by reference.

Although the foregoing invention has been described in some detail by way of illustration and example, for purposes of clarity and understanding it will be understood that certain changes and modifications may be made without departing from the scope or spirit of the invention as defined by the following claims.

What is claimed is:

1. An isolated polynucleotide encoding a polypeptide having DGAT activity, said encoded polypeptide comprising an amino acid sequence selected from the group consisting of:
   at least 330 contiguous residues of the amino acid sequence depicted in SEQ ID NO: 2 or of an amino acid sequence having at least 95% sequence identity therewith; and,
   at least 330 contiguous residues of the amino acid sequence depicted in SEQ ID NO: 4 or of an amino acid sequence having at least 95% sequence identity therewith.

2. The isolated polynucleotide according to claim 1, wherein said encoded polypeptide comprises at least 330 contiguous residues of the amino acid sequence depicted in SEQ ID NO: 2 or of an amino acid sequence having at least 95% sequence identity therewith.

3. The isolated polynucleotide according to claim 1, wherein said encoded polypeptide comprises at least 330 contiguous residues of the amino acid sequence depicted in SEQ ID NO: 2.

4. The isolated polynucleotide according to claim 1, wherein said encoded polypeptide comprises the amino acid sequence depicted in SEQ ID NO: 2.

5. The isolated polynucleotide according to claim 1, said polynucleotide comprising the nucleotide sequence depicted in SEQ ID NO: 1 from nucleotide 82 to nucleotide 1104.

6. The isolated -polynucleotide according to claim 1, wherein said encoded polypeptide comprises at least 330 contiguous residues of the amino acid sequence depicted in SEQ ID NO: 4 or of an amino acid sequence having at least 95% sequence identity therewith.

7. The isolated polynucleotide according to claim 1, wherein said encoded polypeptide comprises at least 330 contiguous residues of the amino acid sequence depicted in SEQ ID NO: 4.

8. The isolated polynucleotide according to claim 1, wherein said encoded polypeptide comprises the amino acid sequence depicted in SEQ ID NO: 4.

9. The isolated polynucleotide according to claim 1, said polynucleotide comprising the nucleotide sequence depicted in SEQ ID NO: 3.

10. A polynucleotide construct comprising a polynucleotide according to claim 1 operably linked to a plant-expressible promoter which is heterologous to said polynucleotide.

11. A vector comprising a polynucleotide according to claim 1.

12. A microbial cell comprising a polynucleotide according to claim 1.

13. The cell according to claim 12, wherein said cell is *Pichia pastoris*.

14. A transgenic plant, plant cell, plant seed, callus, plant embryo, microspore-derived embryo, or microspore, comprising a polynucleotide construct according to claim 10.

15. The transgenic plant, plant cell, plant seed, callus, plant embryo, microspore-derived embryo, or microspore, according to claim 14, which is a canola plant, plant cell, plant seed, plant embryo, or microspore.

16. A method for producing an oil, comprising the steps of:
   (a) growing a transgenic plant according to claim 14; and,
   (b) recovering oil which is produced by said plant.

17. The method according to claim 16, wherein said plant is a canola plant.

18. A method for producing a transgenic plant comprising the steps of:
   (a) introducing into a plant cell or plant tissue a polynucleotide according to claim 1 to produce a transformed plant cell or plant tissue; and,
   (b) cultivating said transformed plant cell or transformed plant tissue to produce said transgenic plant.

19. The method according to claim 18, wherein said transgenic plant is a canola plant.

20. The isolated polynucleotide according to claim 1, wherein said encoded polypeptide comprises at least 340 contiguous residues of the amino acid sequence depicted in SEQ ID NO: 2 or of an amino acid sequence having at least 98% sequence identity therewith.

21. The isolated polynucleotide according to claim 1, wherein said encoded polypeptide comprises at least 340 contiguous residues of the amino acid sequence depicted in SEQ ID NO: 2.

22. The isolated polynucleotide according to claim 1, wherein said encoded polypeptide comprises at least 340 contiguous residues of the amino acid sequence depicted in SEQ ID NO: 4 or of an amino acid sequence having at least 98% sequence identity therewith.

23. The isolated polynucleotide according to claim 1, wherein said encoded polypeptide comprises at least 400 contiguous residues of the amino acid sequence depicted in SEQ ID NO: 4 or of an amino acid sequence having at least 98% sequence identity therewith.

24. The isolated polynucleotide according to claim 1, wherein said encoded polypeptide comprises at least 500 contiguous residues of the amino acid sequence depicted in SEQ ID NO: 4 or of an amino acid sequence having at least 98% sequence identity therewith.

25. The isolated polynucleotide according to claim 1, wherein said encoded polypeptide comprises at least 340 contiguous residues of the amino acid sequence depicted in SEQ ID NO: 4.

26. The isolated polynucleotide according to claim 1, wherein said encoded polypeptide comprises at least 400 contiguous residues of the amino acid sequence depicted in SEQ ID NO: 4.

27. The isolated polynucleotide according to claim 1, wherein said encoded polypeptide comprises at least 500 contiguous residues of the amino acid sequence depicted in SEQ ID NO: 4.

* * * * *